(12) United States Patent
Sutcliffe et al.

(10) Patent No.: US 9,707,231 B2
(45) Date of Patent: Jul. 18, 2017

(54) COMPOSITIONS AND METHODS FOR REDUCTION OF AMYLOID-BETA LOAD

(71) Applicant: Modgene, LLC, Cardiff by Sea, CA (US)

(72) Inventors: J. Gregor Sutcliffe, Cardiff, CA (US); Brian S. Hilbush, San Diego, CA (US)

(73) Assignee: Modgene, LLC, Cardiff by Sea, CA (US)

(*) Notice: Subject to any disclaimer, the term of this patent is extended or adjusted under 35 U.S.C. 154(b) by 87 days.

(21) Appl. No.: 14/354,059

(22) PCT Filed: Nov. 1, 2012

(86) PCT No.: PCT/US2012/063025
§ 371 (c)(1),
(2) Date: Apr. 24, 2014

(87) PCT Pub. No.: WO2013/067157
PCT Pub. Date: May 10, 2013

(65) Prior Publication Data
US 2014/0323496 A1  Oct. 30, 2014

Related U.S. Application Data

(60) Provisional application No. 61/554,375, filed on Nov. 1, 2011, provisional application No. 61/682,031, filed on Aug. 10, 2012.

(51) Int. Cl.
*A61K 31/506* (2006.01)
*A61K 45/06* (2006.01)

(52) U.S. Cl.
CPC .......... *A61K 31/506* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,521,184 A | 5/1996 | Zimmermann et al. | |
| 5,850,003 A | 12/1998 | McConlogue et al. | |
| 6,911,466 B2 | 6/2005 | Koo et al. | |
| 7,638,627 B2 * | 12/2009 | Kankan et al. | 544/331 |
| 7,910,586 B2 | 3/2011 | Netzer et al. | |
| 8,129,370 B2 | 3/2012 | Binder et al. | |
| 2011/0201987 A1 | 8/2011 | Mattner et al. | |

FOREIGN PATENT DOCUMENTS

| | | |
|---|---|---|
| EP | 0564409 | 10/1993 |
| EP | 03703695 | 1/2009 |
| JP | 2006-528206 | 12/2006 |
| JP | 2008-506665 | 3/2008 |
| WO | 99/03854 | 1/1999 |
| WO | 03/057165 | 7/2003 |
| WO | 2004/032925 | 4/2004 |
| WO | 2005/054237 | 6/2005 |
| WO | 2007/019273 | 2/2007 |
| WO | 2007/103683 | 9/2007 |
| WO | 2007/139120 | 12/2007 |
| WO | 2008/128987 | 10/2008 |
| WO | 2010/057020 | 5/2010 |
| WO | WO 2010/057020 A2 * | 5/2010 |
| WO | 2011/016861 | 2/2011 |

OTHER PUBLICATIONS

Muller et al., Structural Modifications of Thalidomide Produce Analogs with Enhanced Tumor Necrosis Factor Inhibitory Activity, J. Med. Chem., 39, 3238-3240, 1996.*
Paris et al., Phenylphenols, biphenols, bisphenol-A and 4-tert-octylphenol exhibit alpha and beta estrogen activities and antiandrogen activity in reporter cell lines, Molecular and Cellular Endocrinology, 193:43-49, 2002.*
PubChem Database, https://pubchem.ncbi.nlm.nih.gov/compound/10239086.*
Barten, et al. "Therapeutic strategies for Alzheimer's disease" Mol Neurobiol 37:171-186, 2008.
Baden, et al. "Gamma-secretase inhibitors for Alzheimer's disease: balancing efficacy and toxicity" Drugs R D, vol. 7:87-97, 2006.
Bassez, et al. "Pleiotropic and diverse expression of ZFHX1B gene transcripts during mouse and human development supports the various clinical manifestations of the "Mowat-Wilson" syndrome" Neurobiol Dis, vol. 15, 240-50 (2004).
Bickel "How to measure drug transport across the blood-brain barrier" NeuroRx. Jan. 2005; 2(1): 15-26.
Blazejczyk, et al. "Ca2+-independent binding and cellular expression profiles question a significant role of calmyrin in transduction of Ca2+-signals to Alzheimer's disease-related presenilin 2 in forebrain" Biochim Biophys Acta 1762, 66-72 (2006).
Bloom, et al. "Mouse models of human neurodegenerative disorders: requirements for medication development" Arch Neurol. 62:185-187, 2005.
Brookmeyer, et al. "Forecasting the global burden of Alzheimer's disease" Alzheimer's Dement 3:186-191, 2007.

(Continued)

*Primary Examiner* — Kortney L Klinkel
*Assistant Examiner* — Tori M Strong
(74) *Attorney, Agent, or Firm* — Casimir Jones, S.C.; Mary Ann Brow

(57) ABSTRACT

The present invention relates to methods and compositions for modulating levels of amyloid-β peptide (Aβ) exhibited by non-neuronal (i.e., peripheral) cells, fluids, or tissues. The invention also relates to modulation of Aβ levels via selective modulation (e.g., inhibition) of γ-secretase activity. The invention also relates to methods of preventing, treating or ameliorating the symptoms of a disorder, including but not limited to an Aβ-related disorder, by administering a compound that results in the modulation of γ-secretase in a non-neuronal tissue, either directly or indirectly to prevent, treat or ameliorate the symptoms of a brain Aβ disorder, such as Alzheimer's disease.

8 Claims, 11 Drawing Sheets

(56) References Cited

OTHER PUBLICATIONS

Buttini, et al. "Modulation of Alzheimer-like synaptic and cholinergic deficits in transgenic mice by human apolipoprotein E depends on isoform, aging, and overexpression of amyloid beta peptides but not on plaque formation" J Neurosci. 22:10539-10548, 2002.

Cedazo-Minguez "Apolipoprotein E and Alzheimer's disease: molecular mechanisms and therapeutic opportunities" J Cell Mol Med. 11:1227-38, 2007.

Cheng et al., "Molecular mechanisms of cardiovascular toxicity of targeted cancer therapeutics," Circ. Res., 2010, 106(1):21-34.

Cheung, et al. "Mechanism of Ca2+ disruption in Alzheimer's disease by presenilin regulation of InsP3 receptor channel gating" Neuron 58, 871-83 (2008).

Chishti, et al. "Early-onset amyloid deposition and cognitive defects in transgenic mice expressing a double mutant form of amyloid precursor protein 695" J. Biol. Chem. 276:21562-21570 (2001).

Chu et al., "Cardiotoxicity associated with tyrosine kinase inhibitor sunitinib," Lancet, 2007, 370:2011-2019.

Dominguez, et al. "Phenotypic and biochemical analyses of BACE1- and BACE2-deficient mice" J Biol Chem 280:30797-30806, 2005.

Doody, et al. "Effect of dimebon on cognition, activities of daily living, behaviour, and global function in patients with mild-to-moderate Alzheimer's disease: a randomised, double-blind, placebo-controlled study" The Lancet 372:207-215 (2008).

Force et al., "Cardiotoxicity of kinase inhibitors: the prediction and translation of preclinical models to clinical outcomes," Nat. Rev. Drug Discov., 2011, 10(2):111-126.

Francis, et al. "aph-1 and pen-2 are required for Notch pathway signaling, gamma-secretase cleavage of betaAPP, and presenilin protein accumulation" 2002, Developmental Cell 3(1): 85-97.

Frank, et al. "A review of antioxidants and Alzheimer's disease" Ann Clin Psychiatry 17(4):269-86 (2005).

Games, et al. "Alzheimer-type neuropathology in transgenic mice overexpressing V717F beta-amyloid precursor protein" Nature 373:523-527 (1995).

Gatti, et al. "Genome-level analysis of genetic regulation of liver gene expression networks" Hepatology 46, 548-57 (2007).

Giacobini "Cholinesterase inhibitors stabilize Alzheimer's disease" Ann NY Acad Sci 920:321-327, 2000.

Hajjar, et al. "Cross-sectional and longitudinal association between antihypertensive medications and cognitive impairment in an elderly population" The Journals of Gerontology Series A: Biological Sciences and Medical Sciences 60:67-73 (2005).

Hansch, et al. "Hydrophobicity and central nervous system agents: on the principle of minimal hydrophobicity in drug design" J. Pharm. Sci. 76(9):663-687 (1987).

Hardy, et al. "The amyloid hypothesis of Alzheimer's disease: progress and problems on the road to therapeutics". Science. 297:353-356, 2002.

He, et al., "Gamma-secretase activating protein is a therapeutic target for Alzheimer's disease," Nature, 2011, 467:95-99.

Hsia, et al. "Plaque-independent disruption of neural circuits in Alzheimer's disease mouse models" Proc Natl Acad Sci U S A. 96:3228-3233, 1999.

Hsiao, et al. "Correlative memory deficits, Abeta elevation, and amyloid plaques in transgenic mice" Science 274:99-102, 1996.

Hu, et al. "Bace1 modulates myelination in the central and peripheral nervous system" Nat Neurosci 9:1520-1525, 2006.

Hustinx, et al. "Differentially expressed genes in pancreatic ductal adenocarcinomas identified through serial analysis of gene expression" Cancer Biol Ther 3, 1254-61 (2004).

International Search Report, mailed Jun. 12, 2012, for International Patent Application No. PCT/US2012/063025, 4 pages.

Ishigaki, et al. "Two novel genes, human neugrin and mouse m-neugrin, are upregulated with neuronal differentiation in neuroblastoma cells" Biochem Biophys Res Commun 279, 526-33 (2000).

Isohata, et al. "Hedgehog and epithelial-mesenchymal transition signaling in normal and malignant epithelial cells of the esophagus" Int J Cancer 125, 1212-21 (2009).

Johnson-Wood, et al. "Amyloid precursor protein processing and A beta42 deposition in a transgenic mouse model of Alzheimer disease" PNAS 94:1550-1555 (1997).

Kawarabayashi, et al. "Age-dependent changes in brain, CSF, and plasma amyloid (beta) protein in the Tg2576 transgenic mouse model of Alzheimer's disease" Neurosci., vol. 21, 372-81 (2001).

Kulnane, et al. "Neuropathological characterization of mutant amyloid precursor protein yeast artificial chromosome transgenic mice" Neurobiol Dis. 8:982-992, 2001.

Laird, et al. "BACE1, a major determinant of selective vulnerability of the brain to amyloid-beta amyloidogenesis, is essential for cognitive, emotional, and synaptic functions" J Neurosci 25:11693-11709, 2005.

Langman, et al. "Risks of bleeding peptic ulcer associated with individual non-steroidal anti-inflammatory drugs" 1994, Lancet 343:1075-1078.

Lehman, et al. "Genetic background regulates beta-amyloid precursor protein processing and beta-amyloid deposition in the mouse" Hum Mol Genet. 12:2949-2956, 2003.

Li, et al. "SEL-10 interacts with presenilin 1, facilitates its ubiquitination, and alters A-beta peptide production" 2002, J. Neurochem. 82(6): 1540-1548.

Luo, et al. "Mice deficient in BACE1, the Alzheimer's beta-secretase, have normal phenotype and abolished beta-amyloid generation" Nat Neurosci 4:231-232, 2001.

Remington's Pharmaceutical Sciences, 15th Ed., Mack Publ. Co., Easton, Pa. 1975, Table of Contents only.

Masliah, et al. "beta-amyloid peptides enhance alpha-synuclein accumulation and neuronal deficits in a transgenic mouse model linking Alzheimer's disease and Parkinson's disease" β amyloid peptides enhance α-synuclein accumulation and neuronal deficits in a transgenic mouse model linking Alzheimer's disease and Parkinson's disease. PNAS 98:12245-12250 (2001).

Milano, et al. "Modulation of notch processing by gamma-secretase inhibitors causes intestinal goblet cell metaplasia and induction of genes known to specify gut secretory lineage differentiation" Toxicol Sci 82:341-358, 2004.

Moasser, et al. "Inhibition of Src kinases by a selective tyrosine kinase inhibitor causes mitotic arrest" Cancer Research 59: 6145-6152 (1999).

Moechars, et al. "Early phenotypic changes in transgenic mice that overexpress different mutants of amyloid precursor protein in brain" J Biol Chem. 274:6483-6492, 1999.

Netzer, et al. "Gleevec inhibits beta-amyloid production but not Notch cleavage" Proc Natl Acad Sci U S A. 100:12444-12449, 2003.

Novartis, Gleevec, Prescribing Information, pp. 1-22 (2003).

Ohno, et al. "Temporal memory deficits in Alzheimer's mouse models: rescue by genetic deletion of BACE1" Eur J Neurosci 23:251-260, 2006.

Ohno, et al. "BACE1 deficiency rescues memory deficits and cholinergic dysfunction in a mouse model of Alzheimer's disease" Neuron 41:27-33, 2004.

Pollack, et al. "Secretase inhibitors for Alzheimer's disease: challenges of a promiscuous protease" Curr Opin Investig Drugs 6:35-47, 2005.

Vardy, et al. "Proteolytic mechanisms in amyloid-beta metabolism: therapeutic implications for Alzheimer's disease" Trends in Molecular Medicine, Elsevier Current Trends, GB LNKDDOI: 10.1016/J.MOLMED.2005.08.004, vol. 11, No. 10, Jan. 1, 2005 (Jan. 1, 2005), pp. 464-472.

Walker, et al. "Data Mining of Gene Expression Changes in Alzheimer Brain" Nat'l Res Council Canada, pp. 1-30 (2003).

Powers "Diagnostic criteria for the neuropathologic assessment of Alzheimer's disease" Neurobiol Aging 18:S53-S54, 1997.

Ramirez, et al. "Prevention of Alzheimer's disease pathology by cannabinoids: neuroprotection mediated by blockade of microglial activation" The Journal of Neuroscience, Feb. 23, 2005, 25(8):1904-1913.

(56) References Cited

OTHER PUBLICATIONS

Richardson, et al. "Ultrastructural and behavioural changes precede amyloid deposition in a transgenic model of Alzheimer's disease" Neuroscience 122:213-228, 2003.
Rojas-Fernandez, et al. "Implications of amyloid precursor protein and subsequent beta-amyloid production to the pharmacotherapy of Alzheimer's disease" Pharmacotherapy 22:1547-1563, 2002.
Ryman, et al. "Genetic loci modulating amyloid-beta levels in a mouse model of Alzheimer's disease" Neurobiol Aging 29:1190-1198, 2008.
Searfoss, et al. "Adipsin, a biomarker of gastrointestinal toxicity mediated by a functional gamma-secretase inhibitor" J Biol Chem 278:46107-46116, 2003.
Selkoe "Alzheimer's disease: genes, proteins, and therapy" Physiol Rev 81:741-766, 2001.
Stabler, et al. "A myristoylated calcium-binding protein that preferentially interacts with the Alzheimer's disease presenilin 2 protein" J Cell Biol., 145, 1277-92 (1999).
Steiner, et al. "PEN-2 is an integral component of the gamma-secretase complex required for coordinated expression of presenilin and nicastrin" 2002, J. Biol. Chemistry: 277(42): 39062-5.
Steiner, et al. "Intramembrane proteolysis by gamma-secretase" J Biol Chem., Jul. 23, 2008, vol. 283, pp. 29627-29631.
Sturchler-Pierrat, et al. "Two amyloid precursor protein transgenic mouse models with Alzheimer disease-like pathology" Proc Natl Acad Sci U S A 94:13287-13292, 1997.
Sutcliffe et al., "Peripheral reduction of beta-amyloid is sufficient to reduce brain beta-amyloid: implications for Alzheimer's disease," Journal of Neuroscience Research, 2010, 89:808-814.
Takayama, et al. "Imatinib mesylate has limited activity against the central nervous system involvement of Philadelphia chromosome-positive acute lymphoblastic leukaemia due to poor penetration into cerebrospinal fluid" Br J Haematol., vol. 119, pp. 106-108, 2002.
Tanzi, et al. "Molecular genetics of Alzheimer's disease and the amyloid beta peptide precursor gene" Ann Med. 21:91-94, 1989.
Terry "Alzheimer's disease and the aging brain" J Geriatr Psychiatry Neurol 19:125-128, 2006.
Uryu, et al. "Repetitive mild brain trauma accelerates Abeta deposition, lipid peroxidation, and cognitive impairment in a transgenic mouse model of Alzheimer amyloidosis" J. Neurosci. 22 (2): 446-54 (2002).
Velpandian, et al. "Development and validation of a simple liquid chromatographic method with ultraviolet detection for the determination of imatinib in biological samples" Journal of Chromatography B, 804(2):431-434 (2004).
Verstappen, et al. "Atypical Mowat-Wilson patient confirms the importance of the novel association between ZFHX1B/SIP1 and NuRD corepressor complex" Hum Mol Genet 17, 1175-83 (2008).
Wang, et al. "WebQTL: web-based complex trait analysis" Neuroinformatics 1, 299-308 (2003).
Waring, et al. "Genome-wide association studies in Alzheimer disease" Arch Neurol. 65:329-34, 2008.
White, et al. "CIB1, a ubiquitously expressed Ca2+-binding protein ligand of the InsP3 receptor Ca2+ release channel" J Biol Chem 281, 20825-33 (2006).
Wisniewski, et al. "Characterization of potent inhibitors of the Bcr-Abl and the c-kit receptor tyrosine kinases" Cancer Research 2002, 62(15):4244-55.
Wolfe "The gamma-secretase complex: membrane-embedded proteolytic ensemble" Biochemistry 45:7931-7939, 2006.
Wong, et al. "Chronic treatment with the gamma-secretase inhibitor LY-411,575 inhibits beta-amyloid peptide production and alters lymphopoiesis and intestinal cell differentiation" J Biol Chem 279:12876-12882, 2004.
Zweier, et al. ""Mowat-Wilson" syndrome with and without Hirschsprung disease is a distinct, recognizable multiple congenital anomalies-mental retardation syndrome caused by mutations in the zinc finger homeo box 1B gene" Am J Med Genet 108, 177-81 (2002).
Australian Patent Examination Report No. 2, Au Patent Application No. 2009313851, mailed Aug. 16, 2013.
Cancino Gonzalo, et al. "STI571 prevents apoptosis, tau phosphorylation and behavioural impairments induced by Alzheimer's beta-amyloid deposits" Brain, vol. 131, No. Part 9, Sep. 2008 (Sep. 2008), pp. 2425-2442.
Dai, et al. "Distribution of STI-571 to the Brain Is Limited by P-Glycoprotein-Mediated Efflux" JPET 304:1085-1092, 2003.
Demattos, et al. "Peripheral anti-Ab antibody alters CNS and plasma Ab clearance and decreases brain Ab burden in a mouse model of Alzheimer's disease" PNAS, 2001 vol. 98, pp. 8850-8855.
Eisele, et al. "Gleevec Increases Levels of the Amyloid Precursor Protein Intracellular Domain and of the Amyloid-β-degrading Enzyme Neprilysin" Molecular Biology of the Cell, vol. 18, 3591-3600, Sep. 2007.
English abstract of JP 2006-528206 retrieved Mar. 7, 2014.
English abstract of JP 2008-506665 retrieved Mar. 7, 2014.
Findeis, et al. "The role of amyloid beta peptide 42 in Alzheimer's disease" Pharmacology and Therapeutics, Elsevier, GB LNKDDOI: 10.1016/J.PHARMTHERA.2007.06.006, vol. 116, No. 2, Sep. 26, 2007 (Sep. 26, 2007), pp. 266-286.
Henley, et al. "Development of semagacestat (LY450139), a functional γ-secretase inhibitor, for the treatment of Alzheimer's disease" Expert Opin. Pharmacother. (2009) 10(10):1657-1664.
Japanese Office Action, JP Patent Application No. 2011-536527, mailed Feb. 4, 2014.
Lee "Aβ immunization: Moving Aβ peptide from brain to blood" PNAS, vol. 98, pp. 8931-8932 (2001).
Martone, et al. "Begacestat (GSI-953): A Novel, Selective Thiophene Sulfonamide Inhibitor of Amyloid Precursor Protein γ-Secretase for the Treatment of Alzheimer's Disease" JPET 331:598-608, 2009.
Matsuoka et al. "Novel Therapeutic Approach for the Treatment of Alzeimer's Disease by Peripheral Administration of Agents with an Affinity to Beta-Amyloid," The Journal of Neuroscience, 2003, vol. 23, No. 1, pp. 29-33.
Netzer, et al., Appeal Brief dated Jun. 29, 2009, U.S. Appl. No. 10/337,261.
Neugroschl, et al. "An Update on Treatment and Prevention Strategies for Alzheimer's Disease" Current Neurology and Neuroscience Reports 2009, 9:368-376.
Pajouhesh, et al. "Medicinal Chemical Properties of Successful Central Nervous System Drugs" NeuroRx, vol. 2, 541-553, Oct. 2005.
Phillips "Is Cancer Drug Right for Alzheimer Disease Too?" Neurology Today, vol. 4, pp. 63-65 (2004).
Remington's Pharmaceutical Sciences, 18th Ed., Mack Publ. Co., Easton, Pa. (1990) pp. 1519-1544.
Suh, et al. "Amyloid Precursor Protein, Presenilins, and α-Synuclein: Molecular Pathogenesis and Pharmacological Applications in Alzheimer's Disease" Pharmacol Rev 54:469-525, 2002.
Tarenflurbil (Flurizan, R-Flurbiprofen) for Alzheimer's disease—mild National Horizon Scanning Centre [retrieved on Aug. 8, 2013] retrieved from the Internet <URL:http://www.hsc.nihr.ac.uk/files/downloads/1404/1909.9c66358bd4cb4f4092b4278d85b0d727.pdf> published Dec. 2007 as per the document.
U.S. Pat. No. 8,129,370 is the English language equivalent of JP 2006-528206.
U.S. Publication No. 2011-0201987 is the English language equivalent of JP 2008-506665.
U.S. Appl. No. 61/114,459, filed Nov. 13, 2008, Sutcliffe, et al.
Van Murum "Current and future therapy in Alzheimer's Disease" Fundamental & Clinical Pharmacology 22 (2008) 265-274.

* cited by examiner

STI-571 ("Gleevec™")     STI-571 Variant ("WGB-BC-15")

Compound 1     Compound 2

*Ngrn*

A.

N-Desmethyl Imatinib

B.

Imatinib Para-diaminomethylbenzene trihydrochloride

C.

Imatinib (Piperidine)-N-oxide

D.

Imatinib (Pyridine)-N-oxide

COMPOSITIONS AND METHODS FOR REDUCTION OF AMYLOID-BETA LOAD

This application is a §371 US National Entry of International Application No. PCT/US2012/063025, filed Nov. 1, 2012, which claims priority to U.S. Provisional Applications Ser. Nos. 61/554,375, filed Nov. 1, 2011, and 61/682,031, filed Aug. 10, 2012, each of which is incorporated herein by reference in its entirety.

FIELD OF THE INVENTION

The present invention relates to methods and compositions for modulating levels of amyloid-β peptide (Aβ) exhibited by non-neural (i.e., peripheral) cells, fluids, or tissues. The invention also relates to modulation of brain Aβ levels via selective modulation (e.g., inhibition) of γ-secretase activity in peripheral tissues. The invention further relates to methods of preventing, treating or ameliorating the symptoms of a disorder, including but not limited to a neural Aβ-related disorder, by peripherally administering a compound that results in the modulation of γ-secretase, either directly or indirectly. The invention also relates to the use of modulators of γ-secretase activity via peripheral administration to prevent, treat or ameliorate the symptoms of Alzheimer's disease. The invention still further relates to the use of inhibitors of Aβ production that have reduced kinase inhibition activity.

BACKGROUND

Amyloid-β (Aβ) peptides are metabolites of the Alzheimer's disease-associated precursor protein, β-amyloid precursor protein (APP), and are believed to be the major pathological determinants of Alzheimer's disease (AD). AD is a neurodegenerative disorder characterized by the age-dependent deposition of Aβ within vulnerable regions of the brain, particularly the frontal cortex and hippocampus (Terry R D. J Geriatr Psychiatry Neurol 19:125-128, 2006). Aβ has a pathogenic effect, leading to progressive neuronal loss that causes deterioration of the ability of those brain regions to orchestrate both higher order and basic neural processes. As the deterioration worsens, the affected individual faces dementia and a worsening quality of life, and eventually the condition is fatal (Brookmeyer R, Johnson E, Ziegler-Graham K, Arrighi H M. Alzheimer's Dement 3:186-191, 2007; Powers J M. Neurobiol Aging 18:S53-S54, 1997).

It is believed that the development of AD is the consequence of the natural biochemical processes associated with aging, and that nearly every individual would eventually manifest symptoms of the disease were he or she to live long enough. Age is the greatest known risk factor for AD with an incidence of 25-50% in people aged 85 years or older (Giacobini E. Ann NY Acad Sci 920:321-327, 2000). For a given individual, the time at which the disorder manifests is the consequence of an additional series of risk factors, some of which might be due to environmental causes, but many of which are due to that individual's genetic endowment: natural variations in the structures and activities of an individual's genes produces ensembles of proteins whose complex webs of interactions render that individual more or less prone to AD. Some of the genes whose protein products affect AD risk have been identified. For example, there are three common variants of the gene that encodes the serum protein Apolipoprotein E, called e2, e3 and e4. Individuals who inherit an e4-encoding allele are at higher risk than average for AD and tend to develop disease at earlier times than individuals with no e4 alleles. Those who inherit e4 alleles from both parents are at even higher risk for early-onset AD, while individuals with e2 alleles are at very low risk, developing the disease later in life than the average if at all (Cedazo-Minguez A. J Cell Mol Med. 11:1227-38, 2007). Traumatic brain injury and repetitive brain trauma have also been found to accelerate brain Aβ deposition and cognitive impairment. Uryu et al. J. Neurosci. 22 (2): 446 (2002).

Most if not all AD is considered to have some genetic component that is linked to the risk threshold for each individual. However, some forms of human AD are particularly highly heritable. These heritable forms are caused by rare mutations in single genes that encode proteins that are associated with this neurodegenerative disorder and that play central roles in the initiation of the disease process. Mutations in these genes can be inherited or can arise sporadically.

One of these genes encodes the Amyloid Precursor Protein (APP) (Tanzi R E. Ann Med. 21:91-94, 1989). APP is a membrane protein whose biochemical function is at present unknown. It is known that APP is a substrate for proteolysis by several endogenous proteases, and that proteolysis liberates fragments having various structures. Two of the protease activities are referred to as β-secretase and γ-secretase. Proteolysis of APP by β-secretase generates a fragment that can subsequently be cleaved by γ-secretase at multiple sites to produce Aβ peptides. γ-secretase is complex of several proteins (including presenilin 1 and presenilin 2), and cleavage of APP by γ-secretase produces multiple isoforms of Aβ, which range from 37 to 43 amino acid residues (see, e.g., Steiner H, Fluhrer R, Haass C., J Biol Chem. 2008 Jul. 23). A 42-residue form of Aβ is thought to be the most pathogenic (Wolfe M S. Biochemistry 45:7931-7939, 2006). The 42-residue Aβ fragment forms oligomeric structures, which, in addition to forming the plaques that deposit in the AD-affected brain, are thought to cause cognitive deficits (Barten D M, Albright C F. Mol Neurobiol 37:171-186, 2008).

Variations in APP that predispose to AD cluster in the vicinity of the proteolytic cleavage sites, affecting the rate at which pathogenic Aβ fragments are generated, their stability, and their ability to form oligomers (Selkoe D J. Physiol Rev 81:741-766, 2001). Individuals inheriting such APP variations usually show signs of AD in their 50s, whereas sporadic AD is not common until individuals reach their 70s (Waring S C, Rosenberg R N. Arch Neurol. 65:329-34, 2008).

The complete molecular identity of γ-secretase enzyme is still unknown. Presenilin 1, or the closely related presenilin 2, is needed for γ-secretase activity. γ-secretase activity is reduced 80% in cultured cells derived from embryos genetically deleted for presenilin 1. All γ-secretase activity is lost in cells lacking both presenilin 1 and presenilin 2. Peptidomimetic inhibitors of γ-secretase activity can be crosslinked to presenilins 1 and 2, suggesting that these proteins are catalytic subunits for the cleavage. However, γ-secretase activity isolated from cells chromatographs as a large complex >1M daltons. Recent genetic studies have identified three more proteins required for γ-secretase activity; nicastrin, aph-1 and pen-1. (Francis et al., 2002, Developmental Cell 3(1): 85-97; Steiner et al., 2002, J. Biol. Chemistry: 277(42): 3906239065; and Li et al., 2002, J. Neurochem. 82(6): 1540-1548). Accumulation of presenilin into high molecular weight complexes is altered in cells lacking these proteins. Rare variations in the genes encoding the presenilin 1 and presenilin 2 components of γ-secretase also confer high risk to early-onset AD (Waring S C, Rosenberg R N. Arch Neurol. 65:329-34, 2008).

A third enzyme, α-secretase, cleaves the precursor protein between the β- and γ-cleavage sites, precluding Aβ production and releasing an approximately 3 kDa peptide known as P3, which is non-pathological. Both β- and α-secretase cleavage also result in soluble, secreted terminal fragments of APP, known as sAPPβ and sAPPα, respectively. The sAPPα fragment has been suggested to be neuroprotective.

As a consequence of these genetic observations and considerable biochemical and neuroanatomical experimentation, the model has emerged that biochemical events that increase the production and accumulation of Aβ, particularly Aβ-42, accelerate the onset and progression of AD. Therapeutic and prophylactic programs, therefore, have been targeted at reducing the production of Aβ or lower its accumulation.

The current focus of AD treatment is lowering of Aβ production and/or accumulation in the brain. Several approaches are presently under investigation (Rojas-Fernandez C H, Chen M, Fernandez H L. Pharmacotherapy 22:1547-1563, 2002; Hardy J, Selkoe D J. Science. 297: 353-356, 2002). Mice that are transgenic for AD-predisposing APP and that additionally carry an inactivating knockout mutation in the β-secretase gene exhibit nearly complete reductions of Aβ in the brain (Luo Y, Bolon B, Kahn S, Bennett B D, Babu-Khan S, Denis P, Fan W, Kha H, Zhang J, Gong Y, Martin L, Louis J C, Yan Q, Richards W G, Citron M, Vassar R. Nat Neurosci 4:231-232, 2001). However, it has been demonstrated that such mice nonetheless exhibit cognitive deficits, premature death, and hypomyelination (Ohno M, Chang L, Tseng W, Oakley H, Citron M, Klein W L, Vassar R, Disterhoft J F. Eur J Neurosci 23:251-260, 2006; Ohno M, Sametsky E A, Younkin L H, Oakley H, Younkin S G, Citron M, Vassar R, Disterhoft J F. Neuron 41:27-33, 2004; Laird F M, Cai H, Savonenko A V, Farah M H, He K, Melnikova T, Wen H, Chiang H-C, Xu G, Koliatsos V E, Borchelt D R, Price D L, Lee H-K, Wong P C. J Neurosci 25:11693-11709, 2005; Dominguez D, Tournoy J, Hartmann D, Huth T, Cryns K, Deforce S, Serneels L, Camacho I E, Marjaux E, Craessaerts K, Roebroek A J, Schwake M, D'Hooge R, Bach P, Kalinke U, Moechars D, Alzheimer C, Reiss K, Saftig P, De Strooper B. J Biol Chem 280:30797-30806, 2005; Hu X, Hicks C W, He W, Wong P, Macklin W B, Trapp B D, Yan R. Nat Neurosci 9:1520-1525, 2006). This leads to the conclusion that β-secretase activity in the brain is necessary for healthy neural function, and therapeutics that lower brain activity of β-secretase might have adverse side effects. In addition, it has been difficult to design potent, brain penetrant β-secretase inhibitors (Barten D M, Albright C F. Mol Neurobiol 37:171-186, 2008), which has been the goal of those who work on the pharmacotherapy of AD.

The effects of γ-secretase inhibitors in reducing brain Aβ have also been investigated. Brain-penetrant γ-secretase inhibitors have been shown to reduce Aβ synthesis and reduce cognitive deficits in mouse models of AD (Barten D M, Meredith J E Jr, Zaczek R, Houston J G, Albright C F. Drugs R D 7:87-97, 2006). However, γ-secretase has targets in addition to APP (Pollack S J, Lewis H. Curr Opin Investig Drugs 6:35-47, 2005), one of which is the Notch family of transmembrane receptors Inhibition of Notch signaling by chronic dosing of γ-secretase inhibitors causes changes in the gastrointestinal tract, spleen, and thymus that limit the extent of Aβ inhibition attainable in vivo using the studied compounds (Searfoss G H, Jordan W H, Calligaro D O, Galbreath E J, Schirtzinger L M, Berridge B R, Gao H, Higgins M A, May P C, Ryan T P. J Biol Chem 278:46107-46116, 2003; Wong G T, Manfra D, Poulet F M, Zhang Q, Josien H, Bara T, Engstrom L, Pinzon-Ortiz M, Fine J S, Lee H J, Zhang L, Higgins G A, Parker E M. J Biol Chem 279:12876-12882, 2004; Milano J, McKay J, Dagenais C, Foster-Brown L, Pognan F, Gadient R, Jacobs R T, Zacco A, Greenberg B, Ciaccio P J. Toxicol Sci 82:341-358, 2004).

U.S. Patent Application 20020128319 A1 states that certain nonsteroidal anti-inflammatory drugs (NSAIDS) lower production and/or levels of Aβ42 in cell cultures expressing Aβ40 and Aβ42 derived from the cleavage of APP. Since there is good evidence that high Aβ42 levels are a major risk factor for AD, such drugs may be useful in preventing, delaying or reversing the progression of AD. The drawback of the use of such drugs, however, is that large doses of NSAIDS are required for significant lowering of Aβ42, and significant gastrointestinal side effects, including bleeding ulcers, are associated with prolonged use of NSAIDS at high doses (Langman et al., 1994, Lancet 343:1075-1078). In addition, there remains an unknown risk for Alzheimer's disease due to amyloid formation from Aβ40 and other forms unaffected by Aβ42 lowering agents. There is, therefore, a need in the art to develop treatments for diseases or disorders related to the regulation of Aβ production.

One class of compounds has been found to reduce Aβ production without affecting Notch signaling. This class of compounds includes the tyrosine kinase inhibitor imatinib mesylate (STI-571, trade name GLEEVEC) and the related compound, 6-(2,6-dichlorophenyl)-8-methyl-2-(methylsulfanylphenyl-amino)-8H-pyrido[2,3-d]pyrimidin-7-one, referred to as inhibitor 2 (Netzer W J, et al., Proc Natl Acad Sci USA. 100:12444-12449, 2003). See also US Patent Publication 2004/0028673 and PCT patent publication WO 2004/032925, each incorporated herein by reference. STI-571 is presently approved for treatment of myelogenous leukemia and gastrointestinal stromal tumors. STI-571 potently reduces the production of Aβ, both in APP-transfected neuroblastoma cells and in cell-free extracts of transfected cells, via a mechanism that does not require the Abl tyrosine kinase, one of the important targets of this drug in leukemia cells (Netzer, supra). STI-571 and a related compound called "Inhibitor 2" were found to reduce production of Aβ in cultures of primary neurons prepared from cerebral cortex of embryonic day 18 rats (Netzer, supra), indicating that these drugs affect proteolytic processing of proteins from both endogenous and transfected APP genes.

STI-571, according to the product literature for GLEEVEC, is administered orally. The drug has been investigated for its effect on Aβ accumulation in brain and the drug has been shown to have poor penetration of the blood-brain barrier. In a STI-571-treated leukemia patient who received the drug, the cerebral spinal fluid (CSF) level of the drug was 92-fold lower than the level in the blood (Takayama N, Sato N, O'Brien S G, Ikeda Y, Okamoto S. Br J Haematol. 119:106-108, 2002). Therefore, its utility in unmodified form as a potential therapeutic for AD has been dismissed (Netzer, supra).

In view of the poor penetration of the blood-brain barrier, researchers investigating the effect of STI-571 on brain Aβ have used implanted osmotic minipumps to deliver STI-571 or inhibitor 2 intrathecally to the brains of guinea pigs (Netzer, supra). While Netzer, et al. observed a decrease in Aβ accumulation in brain, they nonetheless concluded "In the case of Gleevec and related drugs, the ability to achieve a high degree of penetration of the blood-brain barrier would be necessary to improve the likelihood of therapeutic benefit."(Netzer, supra).

In the development of small molecule therapeutics for most diseases, compounds that inhibit protein kinases or block the ATP-binding domain of any enzyme are generally less preferable than compounds exerting the same therapeutic action via alternative mechanisms. Protein kinases regulate a number of essential cellular processes, including cell cycle progression, DNA damage response, cell proliferation, metabolism and cell death, differentiation and survival. Indeed, the human genome contains at least 500 distinct genes encoding protein kinases. The kinase inhibitor drugs, such as imatinib have known off-target interactions that alter their toxicity and side-effect profiles (see, e.g., Force, T. & Kolaja, K. L. Cardiotoxicity of kinase inhibitors: the prediction and translation of preclinical models to clinical outcomes. *Nat. Rev. Drug Discov.* 10, 111-126 (2011)). Imatinib inhibits the kinases Abl, ARG (Abl-related gene protein), PDGF-Ra/B and KIT. The tyrosine kinase inhibitor sunitinib (see e.g., Chu, T. F. et al. Cardiotoxicity associated with tyrosine kinase inhibitor sunitinib. *Lancet* 370, 2011-2019 (2007)) and other kinase inhibitors exhibit cardiotoxicity (see also Cheng, H. & Force, T. Molecular mechanisms of cardiovascular toxicity of targeted cancer therapeutics, *Circ. Res.* 106, 21-34 (2010)). Thus, there is concern that of use of kinase-inhibiting drugs such as imatinib in long-term therapeutic regimens to prevent Alzheimer's disease might have negative consequences that are not observed in relatively brief chemotherapeutic regimens. Even though the reported side effects of imatinib are considered modest for a chemotherapeutic agent used in cancer treatments, it may be expected that new side effects linked to the protein kinase inhibition activity would be observed if tens of millions of people were to take the drug on a maintenance basis.

There remains a need for treatments to effectively reduce the levels of Aβ in brain, and there further remains a need for treatments that effectively reduce levels of Aβ, and that result in less inhibition of Abl kinase activity.

SUMMARY OF THE INVENTION

The present invention relates to methods of treating, preventing or monitoring a brain Aβ disorder, by testing and/or treating peripheral (non-brain, non-CNS) tissues. In some preferred embodiments, the peripheral tissue comprises liver, while in other embodiments, the peripheral tissue comprises blood/and or serum. In some embodiments, the present invention comprises assessing a subject for the presence of AD or predisposition to AD, peripherally administering a compound that modulates accumulation or production of Aβ, and assessing said subject for AD or progression of AD.

The present invention provides methods, compositions and processes related to treatment or prevention of AD by treating the liver of a subject. In particular, the present invention relates to altering Aβ production, processing, accumulation or transport in the liver of a subject by direct inhibition of production (e.g., by inhibition of expression of APP), or by modulating a factor that in turn modulates production, processing, accumulation or transport of Aβ in liver. Such factors include but are not limited to γ-secretase, presenilin 1, presenilin 2, ApoE, calmyrin, neugrin, inositol 1,4,5-trisphosphate receptor (InsP3R) or Smad-interacting protein-1 (SIP1, encoded by Zfhx1b), clusterin (encoded by CLU, also known as ApoJ), phosphoinositol-binding clatherin assembly protein (encoded by PICALM), complement component receptor 1 (encoded by CR1), insulin degrading enzyme (IDE), gamma secretase-activating protein (GSAP), and modulators thereof. The invention encompasses the treatment or prevention of AD by modulation of any factor that, when modulated, influences—either directly (e.g., by acting on APP production or processing) or indirectly (e.g., by acting on a factor that, in turn, acts on a factor that acts on APP), the production of Aβ in liver of a subject. The invention is not limited by the nature of the modulation, or the identity or number of factors acted upon to modulate Aβ in the liver of a subject.

In some embodiments, the present invention provides methods of treating a subject diagnosed with as having a brain Aβ disorder or predisposition to a brain Aβ disorder, comprising peripherally administering a compound that modulates production of Aβ in a peripheral tissue. In some preferred embodiments, the compound inhibits production of Aβ. In particularly preferred embodiments, a peripherally administered compound has a partition coefficient of less than 2.0, more preferably less than 1.5, and still more preferably less than about 1.0. In particularly preferred embodiments, the compound does not substantially cross the blood-brain barrier.

In some embodiments, the present invention provides methods of treating a subject for a brain Aβ disorder or predisposition to a brain Aβ disorder in a subject, comprising peripherally administering a compound that modulates expression of a gene in a peripheral tissue of said subject. In preferred embodiments, modulation of said expression of said gene results in modulation of Aβ production or accumulation in said peripheral tissue. In certain preferred embodiments, the peripheral tissue is the liver of a subject.

The present invention encompasses any method of influencing the production of Aβ in liver, including but not limited to altering expression and/or processing of APP. In some embodiments, the present invention provides methods comprising peripherally administering a compound that modulates expression of one or more of Psen 1, Apo E, InsP3R, Psen2, APP, Cib1, Ngrn, Zfhx1b, CLU (also known as ApoJ), PICALM, IDE, GSAP and CR1 genes. In some embodiments, the methods of the present invention comprises peripherally administering a compound that modulates the activity of one or more of presenilin 2, calmyrin, neugrin, Zfhx1b, clusterin, phosphoinositol-binding clatherin assembly protein, complement component receptor 1, insulin degrading enzyme, GSAP, or APP expression or activity. In some embodiments, one or more of these genes or activities is modulated in the liver of a subject. In some embodiments, modulation comprises inhibition of expression or activity, while in some embodiments, modulation comprises stimulation of expression or activity.

In some embodiments, the present invention comprises a method, e.g., of treating a brain Aβ disorder, comprising the steps of assessing a subject for the presence of a brain Aβ disorder or predisposition to a brain Aβ disorder, peripherally administering a compound that modulates production of Aβ, wherein the compound does not substantially penetrate the blood brain barrier, and assessing the subject for a brain Aβ disorder or progression of a brain Aβ disorder. It is further contemplated that, in some embodiments, the results of the assessment pre and post treatment are compared, to determine, e.g., the effect of treatment on the status of the brain Aβ disorder (e.g., to determine an effect on onset or rate of development or relief of diseases). Modulation of production of Aβ is not limited to any particular means or pathway of modulation. Modulation of production may include, e.g., alteration (e.g., reduction) of expression of APP, or alteration of processing of APP into Aβ.

In some embodiments, the invention comprises the steps of assessing a subject for the presence of a brain Aβ disorder or predisposition to a brain Aβ disorder, peripherally administering a compound that modulates accumulation of Aβ, wherein the compound does not substantially penetrate the blood brain barrier, and assessing the subject for a brain Aβ disorder or progression of a brain Aβ disorder. Modulation of accumulation of Aβ is not limited to any particular means. Modulation of accumulation may include, e.g., decreasing production of Aβ and/or increasing degradation or clearance of Aβ, or alteration of Aβ to produce a modified form with different properties (e.g., a non-pathogenic form).

It is contemplated that in some embodiments of the invention, the modulation of production and/or accumulation of Aβ, the compound administered comprises a modulator of a γ-secretase activity, while in some preferred embodiments, the compound comprises an inhibitor of a γ-secretase activity.

It is further contemplated that in some embodiments of the invention, the modulation of production and/or accumulation of Aβ, the compound administered comprises a modulator of Presenilin 2. In some preferred embodiments, the compound comprises an inhibitor of Presenilin 2. In some embodiments, the compound comprises a modulator of cleavage of amyloid precursor protein, while in some embodiments, the compound comprises an inhibitor of cleavage of amyloid precursor protein. In some embodiments, the compound comprises a composition selected from the group consisting of STI-571, imatinib para-diaminomethylbenzene (e.g., trihydrochloride), N-desmethyl imatinib, Compound 1, Compound 2, LY450139, GSI-953, Flurizan, and E2012 (Eisei) compound, or a blood-brain barrier impermeable variant thereof. In particularly preferred embodiments, the composition has a partition coefficient (e.g., in an octanol/water system) of less than 2.0, more preferably less than 1.5, and still more preferably less than about 1.0. In particularly preferred embodiments, the compound does not substantially cross the blood-brain barrier.

In some embodiments, the compound comprises an interfering oligonucleotide, while in preferred embodiments, the compound comprises interfering RNA. In still more preferred embodiments, the interfering RNA is selected from the group consisting of siRNA, shRNA and miRNA. In some embodiments, the interfering RNA comprises an interfering RNA directed toward amyloid precursor protein RNA, while in other embodiments, the interfering RNA comprises an interfering RNA directed toward Presenilin 2 RNA. In other embodiments the interfering RNA is directed against the Psen 1, Apo E, InsP3R, Cib1, Ngrn, Zfhx1b, CLU (also known as ApoJ), PICALM, IDE, GSAP or CR1 RNA.

It is contemplated that in some embodiments, the compound further comprises a known therapeutic agent for treating, ameliorating, or reducing risk or severity of a brain Aβ-related disorder. In certain preferred embodiments, the known therapeutic agent is selected from the group consisting of cannabinoids, dimebom, prednisone, ibuprofen, naproxyn, indomethacin; statins, selective estrogen receptor molecules, antihypertensives, alpha-blockers, beta-blockers, alpha-beta blockers, angiotensin-converting enzyme inhibitors, angiotensin receptor blockers, calcium channel blockers, diuretics, and antioxidants.

The peripheral administration of said compound in the method of the present invention is not limited to any particular route. Routes of administration include but are not limited to through the eyes (ophthalmic), mouth (oral), skin (transdermal), nose (nasal), lungs (inhalant), oral mucosa (buccal), ear, by injection (e.g., intravenously, subcutaneously, intraperitoneally, etc.) and the like. In certain preferred embodiments, the peripherally administering comprises orally administering.

In some embodiments of the methods of the present invention, the assessing comprises a mental status evaluation. In some preferred embodiments, the assessing comprises one or more of neuropsychological testing and brain imaging.

It is contemplated that in some embodiments, the present invention provides a method of assessing risk of or presence of a brain Aβ disorder in a subject, comprising determining a level of Aβ in a peripheral tissue of said subject. In some other embodiments, the invention provides a method of monitoring a brain Aβ disorder in a subject, comprising determining a level of Aβ in a peripheral tissue of said subject. In some embodiments, the peripheral tissue is blood, while in some embodiments, the peripheral tissue is serum. In some particularly preferred embodiments, monitoring comprises measuring Aβ in said peripheral tissue at a plurality of time points.

In preferred embodiments of the methods disclosed hereinabove, the brain Aβ disorder is Alzheimer's disease.

In some embodiments, the present invention provides methods of monitoring a brain Aβ disorder in a subject comprising analysis of expression or activity of a gene product in peripheral tissue of said subject. In certain preferred embodiments, the gene product is from a gene selected from the group consisting of Psen2, APP, Cib1, Ngrn, and Zfhx1b.

In some embodiments, the present invention provides a method, comprising the steps of assessing a subject for the presence of a brain Aβ disorder or predisposition to a brain Aβ disorder, and peripherally administering a compound that inhibits the transport of peripheral Aβ across the blood brain barrier, wherein said compound is not an anti-Aβ antibody. In preferred embodiments, the further comprises assessing said subject for a brain Aβ disorder or progression of a brain Aβ disorder. In particularly preferred embodiments, the brain Aβ disorder is Alzheimer's disease.

In some embodiments, the present invention provides a method of identifying a genetic target for treatment of a brain Aβ disorder, comprising comparing a liver gene expression profile of offspring from a first parent who has or who is predisposed to said Aβ disorder and a second parent having reduced susceptibility to said Aβ disorder, to identify a heritable genetic marker having a level of expression in liver, wherein increased or decreased expression of said heritable genetic marker in liver of said offspring relative to the level of expression in the liver of said first parent correlates with inheritance of said genetic marker from said second parent.

In some embodiments, the present invention comprises a compound selected from the group consisting STI-571, imatinib para-diaminomethylbenzene, N-desmethyl imatinib, Compound 1, Compound 2, LY450139, GSI-953, Flurizan, and E2012 compound, or a blood-brain barrier impermeable variant thereof, for use in the modulation of production of Aβ in peripheral tissue of a subject having or predisposed to developing a Aβ disorder. In some embodiments, the Aβ disorder is a brain Aβ disorder. In particularly preferred embodiments, the compound has a partition coefficient of less than 2.0, more preferably less than 1.5, and still more preferably less than about 1.0. In particularly preferred embodiments, the compound does not substantially cross the blood-brain barrier.

In some embodiments, the present invention provides a compound selected from the group consisting STI-571, imatinib para-diaminomethylbenzene, N-desmethyl imatinib, Compound 1, Compound 2, LY450139, GSI-953, Flurizan, and E2012 compound, or a blood-brain barrier impermeable variant thereof, for use in the modulation (e.g., inhibition) of production of Aβ in liver of a subject having or predisposed to developing an Aβ disorder. In some embodiments, the Aβ disorder is a brain Aβ disorder. In particularly preferred embodiments, the compound has a partition coefficient of less than 2.0, more preferably less than 1.5, and still more preferably less than about 1.0. In particularly preferred embodiments, the compound does not substantially cross the blood-brain barrier.

In some embodiments, the invention relates to use of a compound selected from the group consisting, imatinib (STI-571), imatinib para-diaminomethylbenzene, N-desmethyl imatinib, WGB-BC-15, Compound 1, Compound 2, LY450139, GSI-953, Flurizan, and E2012 compound, a blood-brain barrier impermeable variant thereof, and/or a pharmaceutically acceptable salt thereof, for the manufacture of a medicament for the modulation of production of Aβ in a peripheral tissue of a subject having or predisposed to developing a brain Aβ disorder In preferred embodiments, the medicament is formulated for oral administration. In particularly preferred embodiments, the peripheral tissue comprises liver. In still more particularly preferred embodiments, the compound has a partition coefficient of less than 2.0, preferably less than 1.5, and still more preferably less than about 1.0. In particularly preferred embodiments, the compound does not substantially cross the blood-brain barrier. In some preferred embodiments, the present invention relates to use of imatinib or a pharmaceutically acceptable salt thereof in the manufacture of a medicament for the inhibition of production of Aβ in liver of a subject having or predisposed to developing a brain Aβ disorder.

The invention also provides for the use of the compounds as described above for the manufacture of a medicament comprising a second therapeutic agent for the treatment of a brain Aβ disorder. In some embodiments, a second therapeutic agent is selected from imatinib (STI-571), imatinib para-diaminomethylbenzene, N-desmethyl imatinib, WGB-BC-15, Compound 1, Compound 2, LY450139, GSI-953, Flurizan, and E2012 compound, a blood-brain barrier impermeable variant thereof, and/or a pharmaceutically acceptable salt thereof. In certain preferred embodiments, the second therapeutic agent comprises one or more agents selected from the group consisting of cannabinoids, dimebom, prednisone, ibuprofen, naproxyn, indomethacin; statins, selective estrogen receptor molecules, antihypertensives, alpha-blockers, beta-blockers, alpha-beta blockers, angiotensin-converting enzyme inhibitors, angiotensin receptor blockers, calcium channel blockers, diuretics, and antioxidants. In certain particularly preferred embodiments of the methods and compositions described above, the compound comprises imatinib para-diaminomethylbenzene and/or N-desmethyl imatinib, or a pharmaceutically acceptable salt thereof.

BRIEF DESCRIPTION OF THE DRAWINGS

FIG. 3A shows Western blots showing levels of Aβ hexamers in plasma from young D2 mice treated with saline vehicle (lanes 1, 2, 9 and 10) or STI-571 at three doses: lanes 3, 4, 11, and 12 show results with 1 mg/kg; lanes 5, 6, 13 and 14 show results with 10 mg/kg; and lanes 7, 8, 15 and 16 show results with 100 mg/kg; n=4 per group. FIG. 3B shows a bar graph quantification of the Western blot images in FIG. 3A. FIG. 3C shows a Western blot showing levels of Aβ hexamers in brain extracts from young B6 mice treated with saline vehicle or STI-571 at 20 mg/kg (n=10 per group in total; only n=5 are shown in Western blot). FIG. 3D shows a bar graph quantification of the Western blot images in FIG. 3C. FIGS. 3E and 3F show bar graphs indicating levels of Aβ hexamers in brain extracts (E) or plasma (F) of old B6 mice treated with saline vehicle or STI-571 at 20 mg/kg (n=4 per group).

DEFINITIONS

Figure 1A:
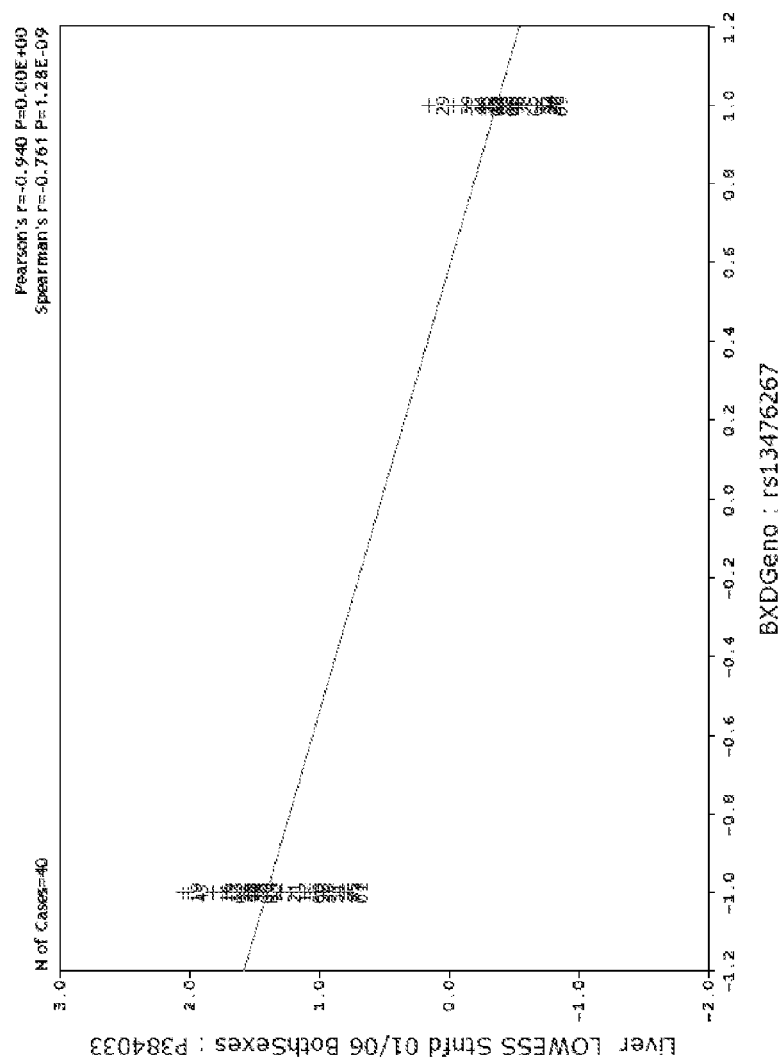
FIG. 1A shows a graph comparing the amount of Psen2 mRNA in liver samples from subject mice, compared to genotype of the mice at the Psen2 locus.
Figure 1B:
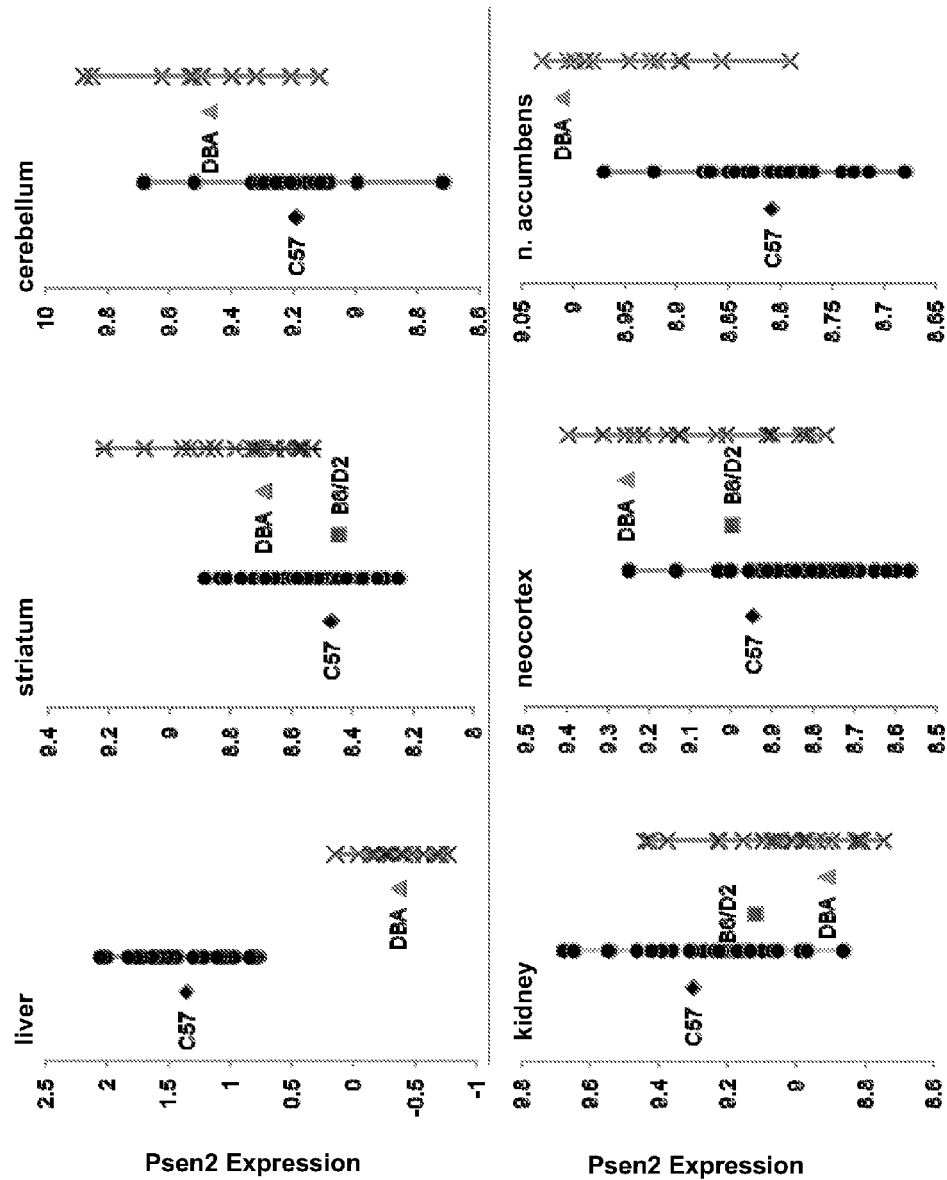
FIG. 1B shows graphs plotting Psen2 locus genotype (B6/B6, B6/D2 or D2/D2) vs. Psen2 mRNA concentration in 6 tissues (arbitrary units) from the up to 89 recombinant inbred (RI) lines. The parental C57 and DBA values are plotted next to those from the RI lines. Some tissues have data from single RI lines that are heterozygous at the Psen2 locus: these are represented on the plots as B6/D2. Data obtained from GeneNetwork.org (J. Wang, R. W. Williams, K. F. Manly K F, Neuroinformatics 1, 299 (2003)). For liver, expression data were initially expressed as the ratio of the liver fluorescence signal to that generated by the reference mRNA sample for each probe. Data were normalized using a robust LOWESS smoothing method that adjusts for non-linearity of signal in the two channels. We then computed the log base 2 of these ratios (median). A value of −1 indicates that expression in liver is roughly ½ that in the control; a value of −2 indicates that expression in the liver is roughly ¼ that in the control, etc. Conversely, a value of +2 indicates that the expression in liver is 4-fold greater in liver. Liver data set from 40 recombinant inbred lines described in by D. Gatti, et al., Hepatology 46, 548 (2007). For other tissues, expression values and alternative normalization methods were as indicated (Wang, supra).
Figure 2:
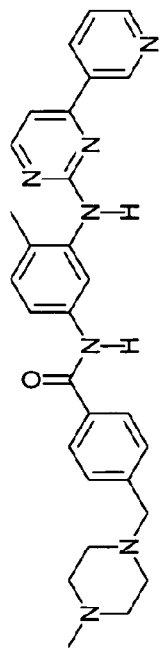
FIG. 2 is a diagram of the chemical structures of STI-571, the mesylate salt GLEEVEC™), STI-571 variant ("WGB-BC-15"), Compound 1 (PD173955, Moasser et al.,1999, Cancer Research 59: 6145-6152; Wisniewski et al., Cancer Research 2002, 62(15):4244-55), and Compound 2 (PD166326; Wisniewski et al., Cancer Research 2002, 62(15):4244-55).
Figure 2:
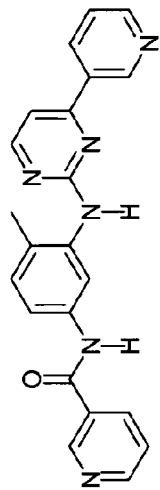
Figure 2:
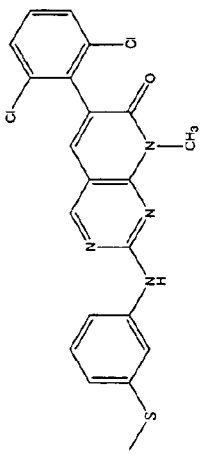
Figure 2:
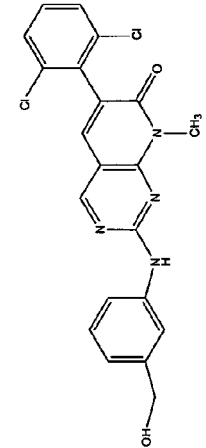

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee, and a human), preferably a human. In one embodiment, the subject is a subject with Alzheimer's disease (AD).

As used herein, the term "Aβ-related disorder" or an "Aβ disorder" is a disease (e.g., Alzheimer's disease) or a condition (e.g., senile dementia) that involves an aberration or dysregulation of Aβ levels. An Aβ-related disorder includes, but is not limited to AD, brain trauma-related amyloid disorders, Down's syndrome and inclusion body myositis.

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease or who has been diagnosed has having a particular disease. It is not intended that the present invention be limited to any particular signs or symptoms, nor disease. Thus, it is intended that the present invention encompasses subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as emotional trauma, physical trauma, malnutrition, industrial hazards, or climate), to specific infective agents (such as worms, bacteria, or viruses), to inherent defect of the organism (such as various genetic anomalies, or to combinations of these and other factors.

As used herein, the terms "subject having AD" or "subject displaying signs or symptoms or pathology indicative of AD" or "subjects suspected of displaying signs or symptoms or pathology indicative of AD" refer to a subject that is identified or diagnosed as having or likely to have AD based on known AD signs, symptoms and pathology.

As used herein, the terms "subject at risk of displaying pathology indicative of AD" and "subject at risk of AD" refer to a subject identified as being at risk for developing AD.

As used herein, the term "AD therapeutic" refers to an agent used to treat or prevent AD. Such agents include, but are not limited to, small molecules, drugs, antibodies, pharmaceuticals, and the like.

As used herein, the term "cognitive function" generally refers to the ability to think, reason, concentrate, or remember. Accordingly, the term "decline in cognitive function" refers to the deterioration of lack of ability to think, reason, concentrate, or remember.

As used herein, the terms "modulate," "modulates," "modulated" or "modulation" shall have their usual meanings, and encompass the meanings of the words "enhance," "promote," "increase," "agonize," "inhibit," "decrease" or "antagonize." A modulator of, e.g., an enzymatic activity, such as an activity of γ-secretase, may act directly, i.e., by direct interaction with the enzyme having the activity to be modulated, or it may act indirectly, i.e., without direct interaction with the enzyme, but via a pathway that results in modulation of the activity.

As used herein, the term "assessing a subject for AD" refers to performing one or more tests to determine, e.g., the presence or progression of AD in a subject, or the risk of development of AD in a subject. Assessing a subject for AD and/or to distinguishing Alzheimer's disease from other causes of memory loss, may comprise evaluating one or more of the following:

1. Medical history, comprising assessing a subject's general health and past medical problems, problems a subject may have in carrying out daily activities
2. Basic medical tests, comprising, e.g., blood tests to rule out other potential causes of the dementia, such as thyroid disorders or vitamin deficiencies.
3. Mental status evaluation, so, e.g., screen memory, problem-solving abilities, attention spans, counting skills and language.
4. Neuropsychological testing, comprising more extensive assessment of memory, problem-solving abilities, attention spans, counting skills and language.
5. Brain scans or imaging, using, e.g., computerized tomography (CT magnetic resonance imaging (MRI); and a positron emission tomography (PET) to look for visible abnormalities.

As used herein, an "agonist" is any compound that acts directly or indirectly on a molecule to produce a pharmacological effect, while an "antagonist" is any compound that acts directly or indirectly on a molecule to reduce a pharmacological effect.

The terms "sample" and "specimen" are used in their broadest sense and encompass samples or specimens obtained from any source. As used herein, the term "sample" is used to refer to biological samples obtained from animals (including humans), and encompasses fluids, solids, tissues, and gases. In some embodiments of the invention, biological samples include neural tissue (e.g., brain tissue) cerebrospinal fluid (CSF), serous fluid, urine, saliva, blood, and blood products such as plasma, serum and the like. However, these examples are not to be construed as limiting the types of samples that find use with the present invention.

As used herein, the term "blood-brain barrier" refers a structure in the central nervous system (CNS) that restricts the passage of various chemical substances and microscopic objects (e.g. bacteria) between the bloodstream and the neural tissue. Directional references to "inside" and "outside" the blood-brain barrier refer to things on the brain/neural tissue side of blood-brain barrier, or the non-brain/neural side of the blood-brain barrier, respectively.

As used herein, the term "blood-brain barrier impermeable variant" as used in reference to a material or compound (e.g., a drug) refers to a variant of a compound having reduced ability to penetrate the blood-brain barrier when administered peripherally to a subject, compare to the penetrability of a parent or reference compound, such that, e.g., the variant does not substantially penetrate the blood-brain barrier of the subject to whom it is administered. As discussed below, the ability of a compound to cross the blood-brain barrier may be characterized any of a number of methods known in the art, e.g., by in vivo or in vitro testing, by computational modeling, or by characterization of a compound (e.g., by physical testing or computational modeling) with respect to features linked to blood-brain barrier transmissibility, e.g., size, charge, etc.

Methods of determining or estimating brain/CNS uptake of drugs include in vivo methods (e.g., intravenous or carotid injection followed by brain sampling or imaging), in vitro methods using, e.g., isolated brain microvessels or cell culture models, and computational (in silico) prediction methods, typically based on factors such as molecular weight and lipophilicity. See, for example, U. Bickel, NeuroRx. 2005 January; 2(1): 15-26, which is incorporated herein by reference, for a review and comparison of methods of measuring drug transport across the blood-brain barrier.

The lipophilicity/hydrophilicity of a compound are generally associated with the rate and extent of entry of a compound into the brain. The lipophilicity/hydrophilicity of a drug is often represented as a partition coefficient representing the behavior of a drug when partitioned in an immiscible organic/aqueous solvent system. An 1-octanol/water partition system has been used extensively in assessing the capability of compounds to cross the blood-brain barrier. The 1-octanol/water partition coefficient, "log P," has been in long standing use as a descriptor of lipophilicity, and computer algorithms providing calculated log P values, like C log P and M log P, often closely match experimentally measured values (within about 0.3 log units; Bickel, supra). For ionizable molecules, the distribution coefficients, i.e., log P values at a defined pH (typically the physiological plasma pH of 7.4) are used. If log P and pKa are known, log D (log distribution coefficient) may be derived using the Henderson-Hasselbalch equation. Log D at pH 7.4 is often quoted to give an indication of the lipophilicity of a drug at the pH of blood plasma.

Hansch and coworkers have determined that drugs with a log P of about 2 will generally find ready entry into the central nervous system (Hansch et al., 1987, J. Pharm. Sci. 76(9):663-687, incorporated herein by reference), and that drugs that are more hydrophilic, such that they have low log P values (e.g., about 1) generally have decreased ability to enter the CNS. This observation has been applied to the modification of drugs to reduce CNS penetration as a means of controlling, e.g., CNS-toxicity or side effects. For example the CNS penetration of heart drug, ARL-57. This drug was considered to be an excellent cardiotonic drug but which could not be used in patients because it caused "spectacular bright color vision" in humans. ARL-57 has a log P=2.59 at pH 8. A more hydrophilic variant of the substance, ARL115, (sulmazole; log P=1.17 at pH 8; calcd. 1.82) was produced and found to lack the CNS side effects, demonstrating that modification of lipophilicity/hydrophilicity can be used as a means of altering, e.g., reducing) drug penetration of the blood-brain barrier (Hansch, et al., supra).

The partition coefficient (log P) of imatinib mesylate has been calculated to be 1.198 and 1.267 at 25 and 37° C., respectively (Velpandian, et al., Journal of Chromatography B, 804(2):431-434 (2004)). This log P value is consistent with the data showing that imatinib does not substantially penetrate the blood-brain barrier.

The terms "peripheral" and "periphera" as used in reference to a location in or on, or a tissue of a subject refer to all locations and tissues of the subject that are outside of the blood-brain barrier.

As used herein, the phrase "does not substantially cross the blood brain barrier" or "does not substantially penetrate the blood brain barrier" relates to material or compounds, e.g., GLEEVEC imatinib mesylate (STI-571) that, if administered in a peripheral tissue or taken orally, either remain absent from a CNS sampling (e.g., in brain tissue, cerebrospinal fluid) altogether, or are present in the CNS sampling at a small percentage of the concentration found in the peripheral tissue, e.g., less than about 10%, preferably less than about 5%, and more preferably less than about 2% of the concentration found in peripheral tissues. For example, GLEEVEC/STI-571 has poor penetration of the blood-brain barrier, as shown in a STI-571-treated leukemia patient whose cerebral spinal fluid (CSF) level of the drug was 92-fold lower than in the blood (Takayama N, Sato N, O'Brien S G, Ikeda Y, Okamoto S. Br J Haematol. 119:106-108, 2002). Thus, GLEEVEC/STI-571 imatinib mesylate does not substantially penetrate the blood brain barrier.

As used herein, the term "effective amount" refers to the amount (e.g., of a composition comprising a modulator of γ-secretase activity of the present invention) sufficient to produce a selected effect. An effective amount can be administered in one or more administrations, applications or dosages and is not intended to be limited to a particular formulation or administration route.

As used herein, a "sufficient amount" of a compound, or "an amount of a compound sufficient to . . . " refers to an amount that contains at least the minimum amount necessary to achieve the intended result. Such an amount can routinely be determined by one of skill in the art based on data from studies using methods of analysis such as those disclosed herein.

As used herein, the term "about" means within 10 to 15%, preferably within 5 to 10%.

As used herein, the terms "manage," "managing" and "management" refer to the beneficial effects that a subject derives from a compound, such as a compound that lowers Aβ levels exhibited by a cell or tissue, which does not result in a cure of the disease. In certain embodiments, a subject is administered one or more such agents to "manage" a disorder so as to prevent or slow the progression or worsening of the disorder.

As used herein, the terms "prevent", "preventing" and "prevention" refer to the impedition of the recurrence or onset of an Aβ-related disorder or one or more symptoms of a Aβ-related disorder in a subject.

As used herein, a "protocol" includes dosing schedules and dosing regimens. The protocols herein are methods of use and include prophylactic and therapeutic protocols.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

"Peripheral administration" refers to any route of administration that is given outside the blood-brain barrier.

As used herein, the terms "co-administration" and "co-administering" refer to the administration of at least two agent(s) (e.g., compositions comprising STI-571, N-desmethyl imatinib, imatinib para-diaminomethylbenzene, and one or more other agents—e.g., an Aβ-related disease therapeutic) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the terms "treat" and "treating" includes administering therapy to prevent, cure, or alleviate/prevent the symptoms associated with, a specific disorder, disease, injury or condition.

As used herein, the term "treatment" or grammatical equivalents encompasses the improvement and/or reversal of the symptoms of disease (e.g., an Aβ-related disease, such as Alzheimer's disease). A compound that causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., an Aβ-related disease, or symptoms or pathologies consistent with an Aβ-related disease) as well as those in which a disease and/or disorder is to be prevented (e.g., using a prophylactic treatment of the present invention).

The term "compound" refers to any chemical entity, pharmaceutical, drug, and the like that can be used to treat or prevent a disease, illness, sickness, or disorder of bodily function. As used herein, a compound may be a single composition (e.g., a pure preparation of a chemical) or it may be a composition comprising a plurality of chemicals (e.g., one or more effective agents and one or more inert agents). A compound may comprise both known and potential therapeutic compositions. A compound can be determined to be therapeutic by screening using the screening methods of the present invention.

A "known therapeutic" compound or agent includes a therapeutic compound that has been shown (e.g., through animal trials or prior experience with administration to humans) to have a therapeutic effect in a treatment. However, a known therapeutic compound is not limited to a compound having a particular level of effectiveness in the treatment or prevention of a disease (e.g., an Aβ-related disease), and includes, e.g., compounds for which data suggests that there is some beneficial effect and little or no negative effect (e.g., compounds that are generally recognized as safe, such as food extracts and nutraceutical compounds). Examples of known therapeutic agents for treating, ameliorating, or reducing risk or severity of Aβ-related diseases (e.g. Alzheimer's disease) when used alone or in combination with other compounds or therapies include, but are not limited to cannabinoids (see, e.g., Ramirez, et al, The Journal of Neuroscience, Feb. 23, 2005, 25(8):1904-1913); dimebom (see, e.g., R S Doody, et al., The Lancet 372:207-215 (2008); anti-inflammatory agents such as prednisone (a steroid) and non-steroidal anti-inflammatory drugs (NSAIDs), including but not limited to ibuprofen, naproxyn, indomethacin; cholesterol-lowering and/or heart protective drugs such as statins, e.g., atorvastatin (LIPITOR®), cerivastatin (BAYCOL®), fluvastatin (e.g., LESCOL®), mevastatin, pitavastatin (e.g., LIVALO®), pravastatin (e.g., PRAVACHOL®), rosuvastatin (e.g., CRESTOR®) and simvastatin (e.g., ZOCOR®); Selective estrogen receptor molecules (SERMs), e.g., raloxifene (EVISTA®); antihypertensives, including alpha-blockers, beta-blockers, alpha-beta blockers, angiotensin-converting enzyme inhibitors, angiotensin receptor blockers (ARBs, such as valsartan (e.g., DIOVAN®)), calcium channel blockers, and diuretics (see, e.g., I Hajjar, et al, *The Journals of Gerontology Series A: Biological Sciences and Medical Sciences* 60:67-73 (2005)); and antioxidants such as garlic extract, curcumin, melatonin, resveratrol, *Ginkgo biloba* extract, green tea, vitamin C and vitamin E (see, e.g., B Frank, et al., Ann Clin Psychiatry 17(4):269-86 (2005).

As used herein, the term "small molecule" generally refers to a molecule of less than about 10 kDa molecular weight, including but are not limited to natural or synthetic organic or inorganic compounds, peptides, (poly)nucleotides, (oligo)saccharides and the like. Small molecules specifically include small non-polymeric (i.e., not peptide or polypeptide) organic and inorganic molecules.

As used herein the term "extract" and like terms refers to a process of separating and/or purifying one or more components from their natural source, or when used as a noun, refers to the composition produced by such a process.

As used herein, the term "kit" refers to any delivery system for delivering materials. In the context of kinase activity or inhibition assays, such delivery systems include systems that allow for the storage, transport, or delivery of reaction reagents and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains standards for comparison to test compounds. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "toxic" refers to any detrimental or harmful effects on a subject, a cell, or a tissue as compared to the same cell or tissue prior to the administration of the toxicant.

As used herein, the term "pharmaceutically purified" refers to a composition of sufficient purity or quality of preparation for pharmaceutical use.

As used herein, the term "purified" refers to a treatment of a starting composition to remove at least one other component (e.g., another component from a starting composition (e.g., plant or animal tissue, an environmental sample etc.), a contaminant, a synthesis precursor, or a byproduct, etc.), such that the ratio of the purified component to the removed component is greater than in the starting composition.

As used herein, the term "pharmaceutical composition" refers to the combination of an active agent (e.g., composition comprising a modulator of γ-secretase activity) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound. In some embodiments of the present invention, a medicament composition comprises a form selected from the group consisting of powder, solution, emulsion, micelle, liposome, gel, and paste form. In some embodiments, a medicament composition comprises a tablet or a filled capsule, wherein said tablet or filled capsule optionally comprises an enteric coating material.

As used herein, the term "excipient" refers to an inactive ingredient (i.e., not pharmaceutically active) added to a preparation of an active ingredient.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "gene expression" and "expression" refer to the process of converting genetic information encoded in a gene into RNA (e.g., mRNA, rRNA, tRNA, or snRNA) through "transcription" of the gene (i.e., via the enzymatic action of an RNA polymerase), and, for protein encoding genes, into protein through "translation" of mRNA. Gene expression can be regulated at many stages in the process. "Up-regulation" or "activation" refer to regulation that increases and/or enhances the production of gene expression products (e.g., RNA or protein), while "down-regulation" or "repression" refer to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cognitive function, amyloid-associated disorder, circulation, hypertension, heart disease, etc.). Test compounds comprise both known and potential therapeutic compounds. A test compound can be determined to be therapeutic by screening using the screening methods of the present invention.

As used herein, a "functional" molecule is a molecule in a form in which it exhibits a property by which it is characterized. By way of example, a functional enzyme is one which exhibits the characteristic catalytic activity by which the enzyme is characterized.

As used herein the term "antisense oligonucleotide" refers to a nucleic acid, e.g., an RNA or DNA segment, that is complementary to the sequence of a target RNA (or fragment thereof). Typically, the target RNA is an mRNA expressed by a cell.

As used herein the term "interfering oligonucleotide" relates to an oligonucleotide capable of inhibiting the function of a target gene product, regardless of the mechanism of inhibition. As used herein, interfering oligonucleotides include but are not limited to antisense oligonucleotides, aptamers, microRNAs (miRNAs), short interfering RNAs (siRNAs) and short hairpin RNAs (shRNAs) Short interfering RNAs typically consist of double-stranded RNA molecules, generally 19-22 nt, while short hairpin RNA, consists of palindromic sequences connected by loop sequences generally 19-29 nt. Methods of producing interfering oligonucleotides are well known to those of skill in the art, and include but are not limited to chemical synthesis, recombinant DNA techniques or generation from larger precursor molecule using enzymatic cleavage, e.g., by Dicer enzymes.

As used herein, the term "antibody" refers to an immunoglobulin or immunoglobulin-derived protein comprising an antigen recognition site. Antibodies include but are not limited to natural or recombinant immunoglobulins comprising two heavy chains and two light chains, as well as modified forms, including, e.g., fragment antibodies and single chain antibodies comprising different combinations of portions of the heavy and light chains. The term encompasses polyclonal and monoclonal antibodies.

As used herein, the term "reduced kinase inhibition imatinib derivative" refers imatinib related compounds having decreased protein kinase activity compared to imatinib, e.g., imatinib para-diaminomethylbenzene and N-desmethyl imatinib. These imatinib derivatives need not be derived from imatinib as a starting material, and the term encompasses, e.g., variants of imatinib that are produced by chemical synthesis.

DETAILED DESCRIPTION OF THE INVENTION

Particular embodiments of the invention are described in this Detailed Description of the Invention, and in the Summary of the Invention, which is incorporated here by reference. Although the invention has been described in connection with specific embodiments, it should be understood that the invention as claimed should not be unduly limited to such specific embodiments. For example, the methods and compositions of the present invention are described in connection with particular modulators of γ-secretase activity, e.g., GLEEVEC (STI-571) imatinib mesylate, and particular brain amyloid disorders (e.g., Alzheimer's Disease). It should be understood that the present invention is not limited to methods or compositions using or comprising imatinib mesylate, or to AD. The present invention relates to the use of reduced kinase inhibition imatinib derivatives in the treatment of Aβ-related disorders.

The present invention is based, in part, on Applicants' surprising discoveries that modulation of Aβ expression or accumulation in peripheral tissues, e.g., in liver, provides therapeutic effect in Aβ-linked diseases of the brain, e.g., Alzheimer's Disease. The present invention, therefore, relates, generally, to methods and compositions for preventing or treating a brain Aβ-related disorder, such as AD, via administration of compounds that modulate the production and/or accumulation of Aβ in non-neural (i.e., peripheral) cells, fluids, and/or tissues.

As discussed above, amyloid-β (Aβ) peptides are metabolites of the amyloid precursor protein (APP), and are believed to be the major pathological determinants of Alzheimer's disease (AD). APP proteolyzed by β and γ-secretase to produce Aβ peptides, with a 42-residue form of Aβ thought to be the most pathogenic. β-secretase is needed for healthy brain function and thus is a poor candidate for inhibition as a means of reducing Aβ. A number of brain-penetrant γ-secretase inhibitors have shown undesirable side-effects as a result of disrupting γ-secretase action on other targets, in particular, the Notch family of transmembrane receptors. One class of compounds has been found to reduce Aβ production without affecting Notch signaling. This class of compounds includes the tyrosine kinase inhibitor imatinib mesylate (STI-571, trade name GLEEVEC) and the related compound, 6-(2,6-dichlorophenyl)-8-methyl-2-(methylsulfanylphenyl-amino)-8H-pyrido[2,3-d]pyrimidin-7-one, referred to as inhibitor 2 (Netzer W J, et al., Proc Natl Acad Sci USA. 100:12444-12449, 2003). However, this class of compounds has been dismissed as a treatment of brain Aβ disorders because it does not cross the blood-brain barrier and is thus prohibitively difficult to deliver to brain tissue.

As noted above, we have discovered that modulation of Aβ production or accumulation in peripheral tissues, e.g., in liver, provides therapeutic effect in Aβ-linked diseases of the brain, e.g., Alzheimer's Disease. The present invention provides methods, compositions and processes related to treatment or prevention of AD by treating the liver of a subject. In particular, the present invention relates to altering Aβ production, processing, accumulation or transport in the liver of a subject by direct inhibition of production (e.g., by inhibition of expression of APP), or by modulating a factor that in turn modulates production, processing, accumulation or transport of Aβ in liver. In preferred embodiments, the inhibition is through the use of compounds that do not substantially cross the blood-brain barrier. In particularly preferred embodiments, compositions and method for treatment comprise the use of a STI-571 or a pharmaceutically acceptable salt thereof, administered peripherally, e.g., orally. In further particularly preferred embodiments, compositions and method for treatment comprise the use of an reduced kinase inhibition imatinib derivative or a pharmaceutically acceptable salt thereof, administered peripherally, e.g., orally. In yet further preferred embodiments, the imatinib derivative is selected from the group consisting of N-desmethyl imatinib and an imatinib para-diaminobenzene composition such as a trihydrochloride.

Use of a Composition in the Manufacture of Medicaments

Imatinib is the generic name [International Non-proprietary Name] for the compound 4-(4-methylpiperazin-1-ylmethyl)-N-[4-methyl-3-(4-pyridin-3-yl)pyrimidin-2-ylamino)phenyl]-benzamide of the following formula I:

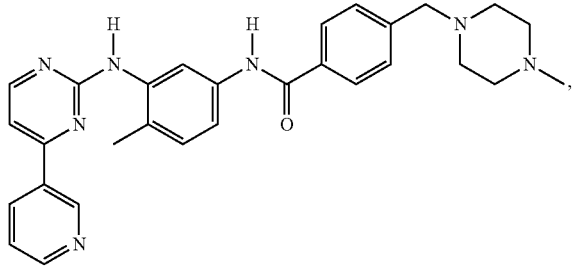

STI-571 generally refers to the mesylate salt of imatinib, and has been approved for the treatment of chronic myeloid leukemia and gastrointestinal stromal tumors. The use of imatinib in the treatment of breast cancer is described in WO 2004/032925. Imatinib, its manufacture, its pharmaceutically acceptable salts, e.g. acid addition salts, and its protein kinase inhibiting properties are described in U.S. Pat. No. 5,521,184, which is hereby incorporated by reference. "Imatinib" corresponds to 4-(4-methylpiperazin-1-ylmethyl)-N-[4-methyl-3-(4-pyridin-3-yl)pyrimidin-2-ylamino)phenyl]-benzamide as either free base or mesylate salt. The preparation of imatinib and the use thereof are described in Example 21 of European patent application EP-A-0 564 409, which is hereby incorporated by reference.

Figure 10:
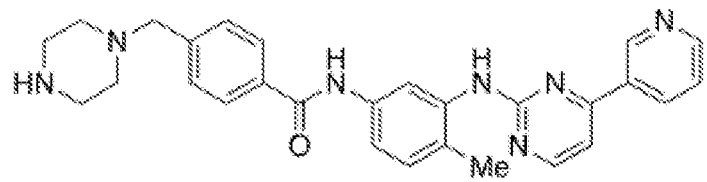
FIGS. 10A-D shows the structures of N-desmethyl imatinib, imatinib para-diaminomethylbenzene 3 HCl, imatinib (pyridine)-N-oxide, and imatinib (piperidine)-N-oxide, respectively.
Figure 10:
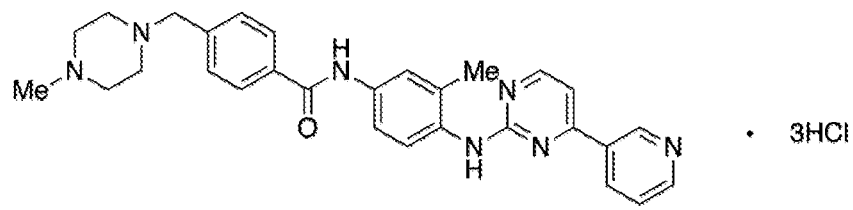
Figure 10:
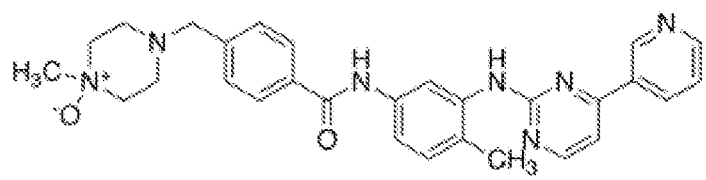
Figure 10:
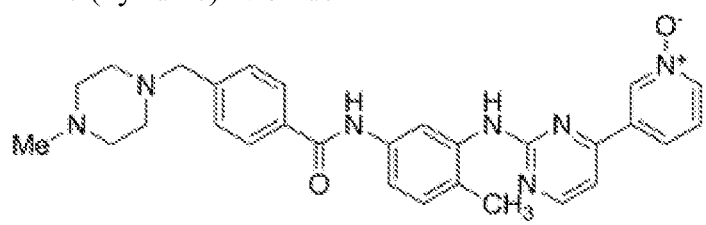

N-desmethyl imatinib, also referred to as N-demethylated piperazine derivate of imatinib is an active metabolite of imatinib having the structure shown in FIG. 10A.

Imatinib para-diaminomethylbenzene is a variant having the structure shown in FIG. 10B.

While peripheral administration is not limited to any particular route of administration, in some preferred embodiments, administration is oral. Thus, in some preferred embodiments, the present invention comprises use of STI-571 and/or a reduced kinase inhibition imatinib derivative in the preparation of an orally administered medicament for the treatment or prevention of a brain Aβ disorder. In some embodiments, the orally administered form comprises a tablet, while in some embodiments, an orally administered form comprises a capsule.

In preferred embodiments, the present invention comprises preparation of a tablet or capsule comprising an effective amount of imatinib and/or reduced kinase inhibition imatinib derivative to reduce Aβ levels in brain. For example, a capsule or tablet may comprise 100 to 1000 mg of an active agent (e.g., imatinib or a derivative thereof). For example, a tablet or capsule may comprise 100, 200, 300, 400, 500, 600, 700, 800, 900, or 1000 mgs, or any convenient dosage amount in between (e.g., 125 mgs, 150 mgs, 175 mgs, 225 mgs, 250 mgs . . . 975 mgs, etc.). In some embodiments, a tablet or capsule is configured to contain a smaller effective dose of imatinib or a reduced kinase inhibition imatinib derivative, e.g., 1 to 5 mg (e.g., 1, 2, 3, 4 or 5 mgs, or a convenient fractional amount thereof), 6 to 10 mgs, 11 to 15 mgs, etc.

Compositions and formulations for oral administration include, for example, powders or granules, suspensions or solutions in water or non-aqueous media, capsules, sachets wafers, dissolvable strips, and tablets. Thickeners, flavoring agents, diluents, emulsifiers, dispersing aids or binders may be desirable. In preferred embodiments, a tablet or capsule (or other form of peripheral administration) is configured to deliver a dose of, or an amount equivalent to any whole integer mg amount between 1 and 1000 mg (e.g., 1, 2, 3, 4, 5, etc.), or any fractional mg amount between 1 and 1000 mg. In certain embodiments, a formulation may comprise, e.g., a capsule filled with a mixture of the composition:

| | |
|---|---|
| Imatinib mesylate (STI-571) | 119.5 mgs (corresponding to 100 mg imatinib free base |
| Cellulose MK GR | 92 mg |
| Crospovidone XL | 15 mg |
| Aerosil 200 | 2 mg |
| Magnesium stearate | 1.5 mg |
| | 230 mg |

In some embodiments, a capsule or tablet comprises an enteric coating. "Enteric" refers to the small intestine, therefore "enteric coating" generally refers to a coating that substantially prevents release of a medication before it reaches the small intestine. While not limiting the invention to any particular mechanism of action, it is understood that most enteric coatings work by presenting a surface that is stable at acidic pH but breaks down rapidly at higher pH.

Compositions and formulations for parenteral administration may include sterile aqueous solutions that may also contain buffers, diluents and other suitable additives such as, but not limited to, carrier compounds and other pharmaceutically acceptable carriers or excipients.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The pharmacokinetics of imatinib mesylate (GLEEVEC) have been evaluated in studies in healthy subjects and in population pharmacokinetic studies. Imatinib is well absorbed after oral administration, with $C_{max}$ achieved within 2-4 hours post-dose. Mean absolute bioavailability is 98%. Following oral administration in healthy volunteers, the elimination half-lives of imatinib and its major active metabolite, the N-desmethyl derivative, are approximately 18 and 40 hours, respectively. Mean imatinib AUC (Area under the plasma drug concentration versus time curve) increases proportionally with increasing doses ranging from 25 mg-1000 mg. There is no significant change in the pharmacokinetics of imatinib on repeated dosing, and accumulation is 1.5-2.5 fold at steady state when dosed once daily. At clinically relevant concentrations of imatinib, binding to plasma proteins in in vitro experiments is approximately 95%, mostly to albumin and al-acid glycoprotein. See, e.g., "Gleevec Prescribing Information" 2003 revision T2003-09; Printed in U.S.A. 89019001 (Novartis).

CYP3A4 is the major enzyme responsible for metabolism of imatinib. Other cytochrome P450 enzymes, such as CYP1A2, CYP2D6, CYP2C9, and CYP2C19, play a minor role in its metabolism. The main circulating active metabolite in humans is the N-demethylated piperazine derivative, N-desmethyl imatinib, formed predominantly by CYP3A4. It shows in vitro potency similar to the parent imatinib. The plasma AUC for this metabolite is about 15% of the AUC for imatinib.

Elimination is predominately in the feces, mostly as metabolites. Based on the recovery of compound(s) after an oral 14C-labeled dose of imatinib, approximately 81% of the dose was eliminated within 7 days, in feces (68% of dose) and urine (13% of dose). Unchanged imatinib accounted for 25% of the dose (5% urine, 20% feces), the remainder being metabolites.

Typically, clearance of imatinib in a 50-year-old patient weighing 50 kg is expected to be 8 L/h, while for a 50-year-old patient weighing 100 kg the clearance will increase to 14 L/h. However, the inter-patient variability of 40% in clearance does not warrant initial dose adjustment based on body weight and/or age but indicates the need for close monitoring for treatment related toxicity.

As in adult patients, imatinib was reportedly rapidly absorbed after oral administration in pediatric patients, with a Cmax of 2-4 hours. Apparent oral clearance was similar to adult values (11.0 L/hr/m2 in children vs. 10.0 L/hr/m2 in adults), as was the half-life (14.8 hours in children vs. 17.1 hr in adults). Dosing in children at both 260 mg/m2 and 340 mg/m2 achieved an AUC similar to the 400-mg dose in adults. The comparison of AUC(0-24) on Day 8 versus Day 1 at 260 mg/m2 and 340 mg/m2 dose levels revealed a 1.5 and 2.2-fold drug accumulation, respectively, after repeated once daily dosing. Mean imatinib AUC did not increase proportionally with increasing dose. "Gleevec Prescribing Information" 2003 revision T2003-09; Printed in U.S.A. 89019001 (Novartis).

Although modulation of Aβ production in liver by treatment with imatinib is used as an example above, the present invention is not limited to treatment of the liver with this compound, and provides general methods of treating a subject for a brain Aβ disorder or predisposition to a brain Aβ disorder in a subject, comprising peripherally administering a compound that modulates expression of a gene in a peripheral tissue of said subject. In preferred embodiments, modulation of said expression of said gene results in modulation of Aβ production or accumulation in said peripheral tissue. In certain preferred embodiments, the peripheral tissue is the liver of a subject.

In particularly preferred embodiments, the modulation of Aβ production comprises use of a composition that has reduced protein kinase inhibition activity compared to, e.g., imatinib.

As described in Example 3, below, the present invention provides compositions that inhibit the formation of Aβ while exhibiting substantially reduced protein kinase inhibition compared to imatinib. In particular, present invention provides preparations of imatinib para-diaminomethylbenzene and/or N-desmethyl imatinib for use in the reduction of Aβ loads in treated cell and subjects.

The present invention encompasses any method of influencing the production of Aβ in liver, including but not limited to altering expression and/or processing of APP. In some embodiments, the present invention provides methods comprising peripherally administering a compound that modulates expression of one or more of Psen 1, Apo E, InsP3R, Psen2, APP, Cib1, Ngrn, Zfhx1b, CLU (also known as ApoJ), PICALM, IDE, GSAP, and CR1 genes. In some embodiments, the methods of the present invention comprises peripherally administering a compound that modulates the activity of one or more of presenilin 2, calmyrin, neugrin, Zfhx1b, clusterin, phosphoinositol-binding clatherin assembly protein, complement component receptor 1, insulin degrading enzyme, GSAP, or APP expression or activity. In some embodiments, one or more of these genes or activities is modulated in the liver of a subject. In some embodiments, modulation comprises inhibition of expression or activity, while in some embodiments, modulation comprises stimulation of expression or activity.

Assessing and Monitoring Brain Aβ Disorders During Peripheral Treatment

The present invention relates to testing for and treatment of AD and AD risk by testing of and administration to peripheral (i.e., non-brain) tissues of a subject. As discussed below, the present study demonstrates that presenilin 2 expression in the liver and/or in one or more peripheral tissues modifies Aβ accumulation, and that reduction of Aβ in the periphery is sufficient to modify its deposition in the brain. Thus, despite extensive teaching in the literature to the contrary, an effective therapeutic or prophylactic treatment for AD that reduces Aβ accumulation need not cross the blood-brain barrier and enter the brain. Inhibition of Psen2 or γ-secretase activity, or reduction of Aβ production or accumulation by other means, outside of the central nervous system (i.e., outside the blood-brain barrier) finds application in the protection of the brain from Aβ-related pathologies. Treatment of peripheral tissues has the additional benefit of protecting the brain from any adverse side effects that could occur were the therapeutic to enter the brain.

In some embodiments, the present invention provides methods of tailoring treatments to the biochemical status of a subject or patient. It is contemplated that features of effective doses of one or more of compounds selected for the modulation of Aβ in a peripheral tissue may be affected by the particular biochemical circumstances of a subject or patient, including but not limited to the presence of other drugs or medications (e.g. for treatment of an Aβ disorder or unrelated conditions), or biochemical changes caused by other circumstances. The present invention provides methods comprising monitoring a subject by assessing said subject for a brain Aβ disorder or progression of a brain Aβ disorder before and after administration of a compound that modulates production of Aβ, e.g., in liver. In some embodiments, therapy for a brain Aβ disorder is selected, adjusted, or altered accordingly.

EXPERIMENTAL EXAMPLES

The following examples are provided in order to demonstrate and further illustrate certain preferred embodiments and aspects of the present invention and are not to be construed as limiting the scope thereof.

Example 1

Identification of Modifiers of the Development of AD-like Pathology

Transgenic mouse models have been developed that recapitulate critical features of human Alzheimer's disease. The APP gene carrying some of the variations that are AD-predisposing in humans have been joined to various transcriptional promoters and introduced into the mouse germ line (Games D, Adams D, Alessandrini R, Barbour R, Berthelette P, Blackwell C, Carr T, Clemens J, Donaldson T, Gillespie F, et al. Nature 373:523-527; Hsia A Y, Masliah E, McConlogue L, Yu G Q, Tatsuno G, Hu K, Kholodenko D, Malenka R C, Nicoll R A, Mucke L. Proc Natl Acad Sci USA. 96:3228-3233, 1999; Hsiao K, Chapman P, Nilsen S, Eckman C, Harigaya Y, Younkin S, Yang F, Cole G. Science 274:99-102, 1996; Sturchler-Pierrat C, Abramowski D, Duke M, Wiederhold K H, Mistl C, Rothacher S, Ledermann B, Bürki K, Frey P, Paganetti P A, Waridel C, Calhoun M E, Jucker M, Probst A, Staufenbiel M, Sommer B. Proc Natl Acad Sci USA 94:13287-13292, 1997; Moechars D, Dewachter I, Lorent K, Reverse D, Baekelandt V, Naidu A, Tesseur I, Spittaels K, Haute C V, Checler F, Godaux E, Cordell B, Van Leuven F. J Biol Chem. 274:6483-6492, 1999; Richardson J C, Kendal C E, Anderson R, Priest F, Gower E, Soden P, Gray R, Topps S, Howlett D R, Lavender D, Clarke N J, Barnes J C, Haworth R, Stewart M G, Rupniak H T. Neuroscience 122:213-228, 2003; Buttini M, Yu G Q, Shockley K, Huang Y, Jones B, Masliah E, Mallory M, Yeo T, Longo F M, Mucke L. J Neurosci. 22:10539-10548, 2002). The resulting transgenic mice develop Aβ deposits, but the timing varies from 3 months to 15 months of age. The variables responsible for these age differences include the particular transcriptional promoter chosen, the particular AD-predisposing mutations in the APP gene, the chromosomal site of transgene integration and the mouse background strain on which the transgene is perpetuated (reviewed in Bloom F E, Reilly J F, Redwine J M, Wu C C, Young W G, Morrison J H. Arch Neurol. 62:185-187, 2005).

One report (Kulnane L S, Lamb B T. Neurobiol Dis. 8:982-992, 2001) introduced R1.40, a human APP transgene carrying the so-called Swedish mutations (K670N, M671L, variations that predispose those humans that inherit this mutated gene to develop early-onset AD) into a mixed C57B1/6x129/Sv mouse genetic background. Expression of the R1.40 transgene was driven from the natural human APP promoter. Aβ deposits were first detectable in brains of these mice at 14-16 months. Subsequently, the R1.40 transgene was crossed from its initial background separately into C57B1/6 (B6), DBA/2 (D2) and 129/Sv backgrounds. Then, each of these 3 strains was bred to congeneity: 10 or more back-crosses into the same background so that 3 transgenic strains with uniform but distinct backgrounds were created (Lehman E J, Kulnane L S, Gao Y, Petriello M C, Pimpis K M, Younkin L, Dolios G, Wang R, Younkin S G, Lamb B T. Hum Mol Genet. 12:2949-2956, 2003). Although all three transgenic strains produced the same amount of APP precursor (indicating that the transgene was expressed comparably in the 3 strain backgrounds), B6s accumulated more Aβ (the pathogenic fragment of APP) as measured by ELISA on brain homogenates and plasma at 21 and 60 days than the other 2 strains, and developed amyloid deposits characteristic of human AD at 13.5 months, while the D2s were protected (no deposits at 2 years). Thus, this indicates that there are genes that distinguish B6 and D2 mice and that modify the development of AD-like pathology, and most likely these are involved in the accumulation of the pathogenic substance Aβ (Lehman E J, Kulnane L S, Gao Y, Petriello M C, Pimpis K M, Younkin L, Dolios G, Wang R, Younkin S G, Lamb B T. Hum Mol Genet. 12:2949-2956, 2003). The identities of the modifier genes might suggest therapeutic or prophylactic modalities that would mimic the modifier effect and delay or prevent the emergence of AD pathology.

So as to assign the modifying genes to chromosomal intervals, Ryman and colleagues (Ryman D, Gao Y, Lamb B T. Neurobiol Aging 29:1190-1198, 2008) crossed female B6 R1.40 mice (homozygous for the transgene) with male D2 R1.40 mice (also homozygous for the transgene), then crossed their F1 offspring (all of which had 2 copies of the R1.40 transgene) to non-transgenic B6xD2 F1 offspring, generating 516 F2 mice, each of which carried a single transgene. These were genotyped with 909 SNPs. Aβ was measured by ELISA in brain homogenates from the 516 mice. Regression analysis correlating the amount of Aβ accumulation with the genotypes of the 516 mice allowed 3 modifying loci to be assigned to broad regions centered on the following positions: chromosome 1, 182.049374 Megabases (Mb); chromosome 2, 41.216315 Mb; chromosome 7, 63.680922 Mb.

Identifying a Modifier Gene

The mouse gene encoding presenilin 2, Psen2, is located on chromosome 1 at 182.06371 Megabases, the center of the trait locus interval, suggesting it as a candidate for modifying Aβ accumulation and deposit. This is consistent with its function as a component of γ-secretase. For Psen2 to represent the actual modifier mapped to chromosome 1 by Ryman and colleagues, its activity must vary heritably (in a Mendelian fashion) between B6 and D2 mouse strains, and the Psen2 activity must be greater in B6 mice than D2 mice, because lower γ-secretase activity would be expected to be protective in AD. We investigated this issue by determining the amount of mRNA that accumulates from the Psen2 gene in various tissues in B6 and D2 mouse strains and up to 89 strains of recombinant inbred mice produced by crossing B6 and D2 mice and breeding the offspring to congeneity. The concentrations of each of more than 20,000 mRNAs in 10 tissues (brain, cerebellum, liver, striatum, kidney, hippocampus, eye, prefrontal cortex, nucleus accumbens and neocortex) of B6 and D2 mouse strains and the 89 recombinant inbred mouse strains are available in public databases compiled at http://www.GeneNetwork.org. For each of the 89 recombinant inbred mouse strains, it has been determined by genotyping whether the strain has inherited each interval of its genome from the B6 or D2 parent.

Probe rs13476267 is located on chromosome 1 at 182.120454 Mb. Using the software on the world wide web public site at genenetwork.org/webqtl/WebQTL.py, we performed trait correlations between the genotype of the rs13476267 interval and the amount of Psen2 mRNA that accumulates in each of the 10 tissues in the up to 89 recombinant inbred mice, calculating the Pearson's product-moment. The values were:

| | |
|---|---|
| brain | $|r| < 0.05$ |
| cerebellum | $r = 0.6344$ |
| liver | $r = -0.9402$ |
| striatum | $r = 0.5329$ |
| kidney | $r = -0.4733$ |
| hippocampus | $|r| < 0.36$ |
| eye | $|r| < 0.35$ |
| prefrontal cortex | $|r| < 0.51$ |
| nucleus accumbens | $r = 0.7260$ |
| neocortex | $r = 0.5500$ |

None of the tissue samples derived from brain shows high heritability ($|r|>0.9$) of Psen2 expression, and for the two brain regions that exhibit modest heritability of Psen2 mRNA expression, cerebellum and nucleus accumbens, more Psen2 mRNA was correlated with the D2 genotype than the B6 genotype. Thus, Psen2 expression in the brain is not a modifier of Aβ accumulation. However, in the liver, the amount of Psen2 mRNA was highly correlated with the genotype at the Psen2 locus (FIG. 1A). Furthermore, B6 mice express more Psen2 mRNA than do D2 mice.

The data demonstrate that Psen2 expression in the liver or in one or more peripheral tissues modifies Aβ accumulation, and that reduction of Aβ in the periphery is sufficient to modify its deposition in the brain. Thus, despite extensive teaching in the literature to the contrary, based at least in part on the natural assumption that a brain disease would be caused by events that occur within the brain, an effective therapeutic or prophylactic treatment for AD that reduces Aβ accumulation need not cross the blood-brain barrier and enter the brain. Inhibition of Psen2 or γ-secretase activity, or reduction of Aβ production or accumulation by other means, outside of the central nervous system, is sufficient to protect the brain from Aβ deposition while protecting the brain from adverse side effects that might occur were the therapeutic to enter the brain. Treatment of Aβ accumulation in the periphery can be accomplished by using routes of drug delivery that do not comprise direct application to the CNS (e.g., by CSF delivery), such as via oral administration.

Example 2

Peripheral Administration of STI-571 Imatinib Mesylate to Reduce Aβ in Brain

The data from the mapping studies and our further ideas suggested a novel therapeutic route to treat AD (its initiation, progression or severity) based on modulating Aβ production in liver. The basis of a new therapeutic strategy is that a drug that lowers steady-state levels of Aβ in blood (by inhibiting production of Aβ in liver) would lower Aβ concentrations in the brain.

An experiment was designed to test the effect of STI-571 imatinib mesylate administration on Aβ protein levels in brain and blood tissue in 2 strains of mice. Mice were administered STI-571 imatinib mesylate by IP injection over the course of one week and brain and tissue samples removed and Aβ protein levels measured by ELISA or Western blot.

Wild-type C57Bl/6 and DBA/2J male mice (age 8-12 weeks) were administered drug or vehicle twice daily for 7 days by intraperitoneal injection. Vehicle groups (n=4 animals per strain) were injected with 100 ul of saline and drug treatment groups (n=4) received 1, 10 or 100 mg/kg STI-571 (GLEEVEC imatinib, methanesulfonate salt, Catalog No. 1-5508, LC laboratories, Woburn, Mass.). The STI-571 dose prescribed for human cancer patients is 100 mg to 1000 mg. See, for example, Gleevec Prescribing Information 2003 revision T2003-09; Printed in U.S.A. 89019001 (Novartis), incorporated herein by reference.

Animals were sacrificed 12 hr after the last injection. Individual mice were anesthetized with isoflurane and blood samples (100-300 ul) taken by cardiac puncture with heparinized syringes. Samples were placed on ice for 30 minutes in the presence of EDTA and then centrifuged for 20 minutes at 16,000×g at 4° C. The plasma fraction was removed and stored at −80° C. Brains were removed and frozen rapidly on dry ice and stored at −80° C.

Detection of mouse $A\beta_{1-40}$ in blood and brain samples was performed by using a commercially available immunoassay kit (Biosource mouse $A\beta_{1-40}$, Catalog No. KMB3481, Invitrogen, Carlsbad, Calif.) or by Western blot. Mouse brain samples were prepared by homogenizing brain tissue in a polytron in the presence of 5M guanidine HCl and 50 mM Tris HCl, pH 8.0 as described in the assay protocol. (see, e.g., Masliah, E., et al., (2001) β amyloid peptides enhance α-synuclein accumulation and neuronal deficits in a transgenic mouse model linking Alzheimer's disease and Parkinson's disease. PNAS 98:12245-12250; Johnson-Wood, K, et al. (1997) Amyloid precursor protein processing and A beta42 deposition in a transgenic mouse model of Alzheimer disease PNAS 94:1550-1555; and Chishti, M. A., et al. (2001); Early-onset amyloid deposition and cognitive defects in transgenic mice expressing a double mutant form of amyloid precursor protein 695. J. Biol. Chem. 276:21562-21570.)

For the assay, brain homogenates were diluted 1:10 in a reaction buffer containing Dulbecco's phosphate buffered saline with 5% BSA and 0.03% Tween-20, supplemented with protease inhibitor cocktail (Catalog No. 539131, EMD Biosciences, La Jolla, Calif.). Blood samples were diluted 1:5 in standard diluent buffer. Samples were assayed in duplicate and OD450 measured on a Tecan infinite 2000 plate reader.

Oligomeric Aβ was extracted in the SDS fraction essentially as described (T. Kawarabayashi, et al., Neurosci 21, 372 (2001)). For Western blots, samples were subjected to P AGE analysis, transferred to PVDF membranes and the Aβ hexamers were visualized using a monoclonal antibody 4G8 directed against mouse Aβ (1:1,000; Covance) using the manufacturer's recommended protocol. Blots were scanned by densitometry, and then reprobed with an antibody to histone H3 (1:50,000; Abcam) as a loading and transfer control. Data are depicted as normalized optical density.

Levels of Aβ in both the brain and blood differed between the two strains of mice (C57B1/6 and DBA/2J) tested. The levels of Aβ were higher in both brain and blood samples from C57B1/6 mice compared to DBA/2J in the vehicle-treated control groups, as was shown previously.

Figure 3:
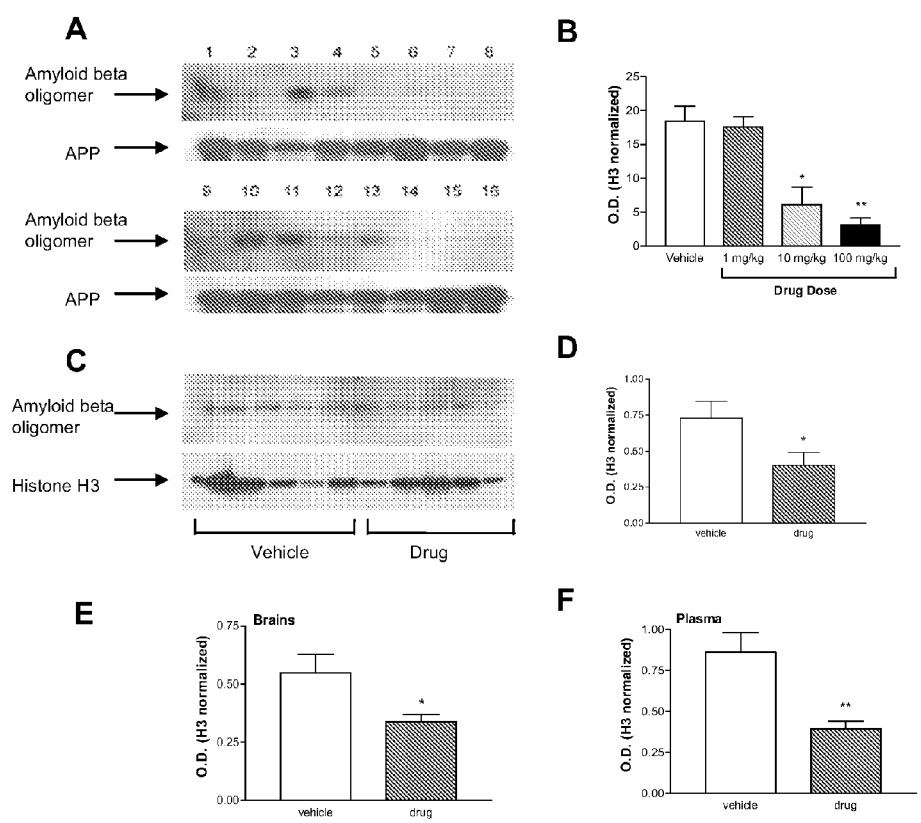
FIGS. 3A-3F show the effects of peripherally administered STI-571 on the levels of Aβ in plasma and whole brain. Wild-type B6 and D2 mice (age 8-12 weeks [A-F]or 15-18 months[G, H]) were administered drug or vehicle twice daily for 7 days by intraperitoneal injection.

FIG. 3 shows the effects of peripherally administered STI-571 on the levels of Aβ in plasma and brain. FIG. 3A shows Western blots showing levels of Aβ hexamers in plasma from young D2 mice treated with saline vehicle (lanes 1,2, 9 and 10) or STI-571 at three doses: lanes 3, 4, 11, and 12 show results with 1 mg/kg; lanes 5, 6, 13 and 14 show results with 10 mg/kg; and lanes 7, 8, 15 and 16 show results with 100 mg/kg; n=4 per group. FIG. 3B shows a bar graph quantification of the Western blot images in FIG. 3A. FIG. 3C shows a Western blot showing levels of Aβ hexamers in brain extracts from young B6 mice treated with saline vehicle or STI-571 at 20 mg/kg (n=10 per group in total; only n=5 are shown in Western blot). FIG. 3D shows a bar graph quantification of the Western blot images in FIG. 3C. FIGS. 3E and 3F show bar graphs indicating levels of Aβ hexamers in brain extracts (E) or plasma (F) of old B6 mice treated with saline vehicle or STI-571 at 20 mg/kg (n=4 per group).

A dose-dependent reduction in plasma Aβ was observed (FIG. 3A-B), and the highest dose reduced circulating Aβ by approximately 75%. An intermediate dose, 20 mg/kg, was selected for study of brain effects. This dose reduced brain and plasma levels of Aβ by approximately 50% in young and old B mice (FIGS. 3B and 3C). These levels of Aβ have been observed to be protective in the R1.40 mouse model (E. J. Lehman, et al., Hum Mol Genet 12, 2949 (2003)).

These results demonstrate that short-term (one week) STI-571 imatinib mesylate treatment significantly lowers Aβ levels in the blood and brain. Furthermore, as the drug does not cross the blood-brain barrier appreciably at the concentrations used in this study, the results indicate that STI-571 imatinib mesylate can indirectly alter brain Aβ levels by modulating Aβ production peripherally.

Example 3

Identification of Candidate Chromosome 2 And 7 Modifier Genes

The studies described above demonstrate that pathogenic Aβ likely derives from the liver. Using the same database and methodology described above, we also searched for genes that map into the chromosomes 2 and 7 intervals, and whose activities in the liver varied heritably between B6 and D2 mouse strains.

Figure 4:
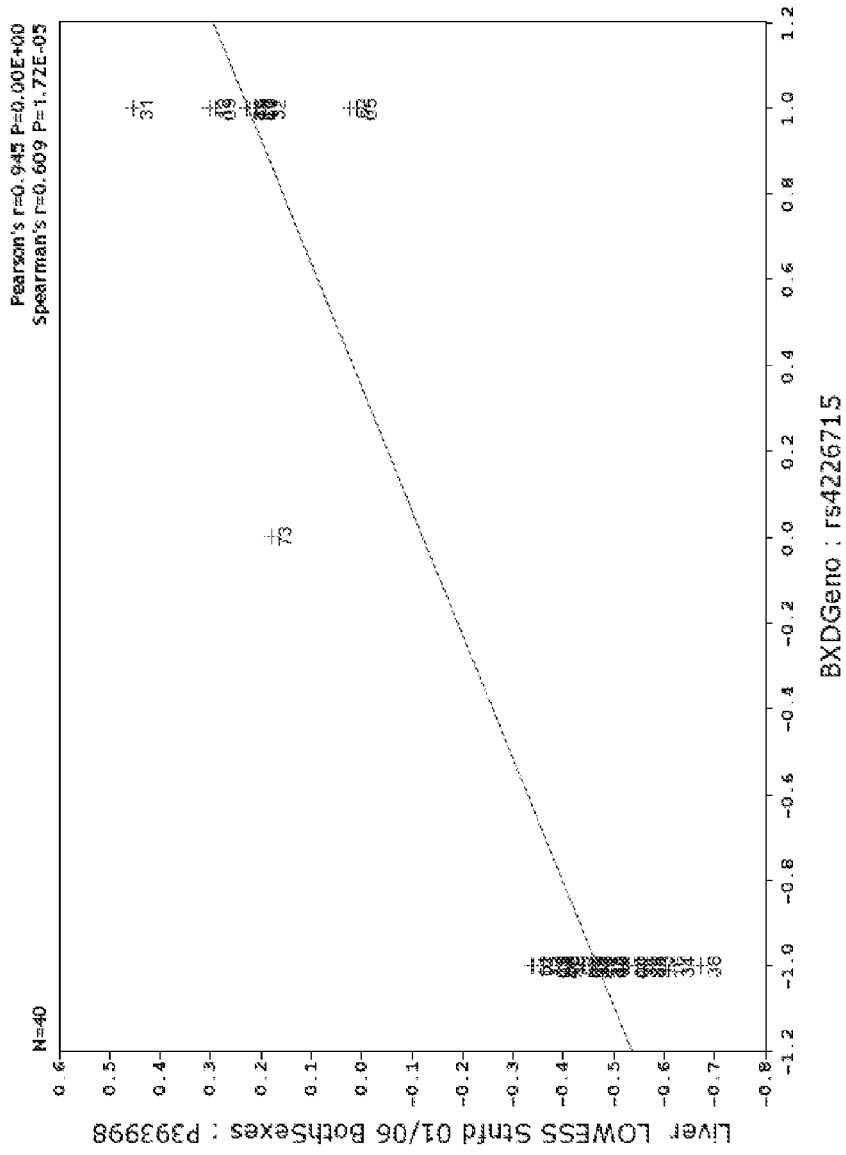
FIG. 4 shows a graph comparing the amount of Ngrn mRNA in liver samples from subject mice, compared to the genotype of the mice at the Ngrn locus.
Figure 5:
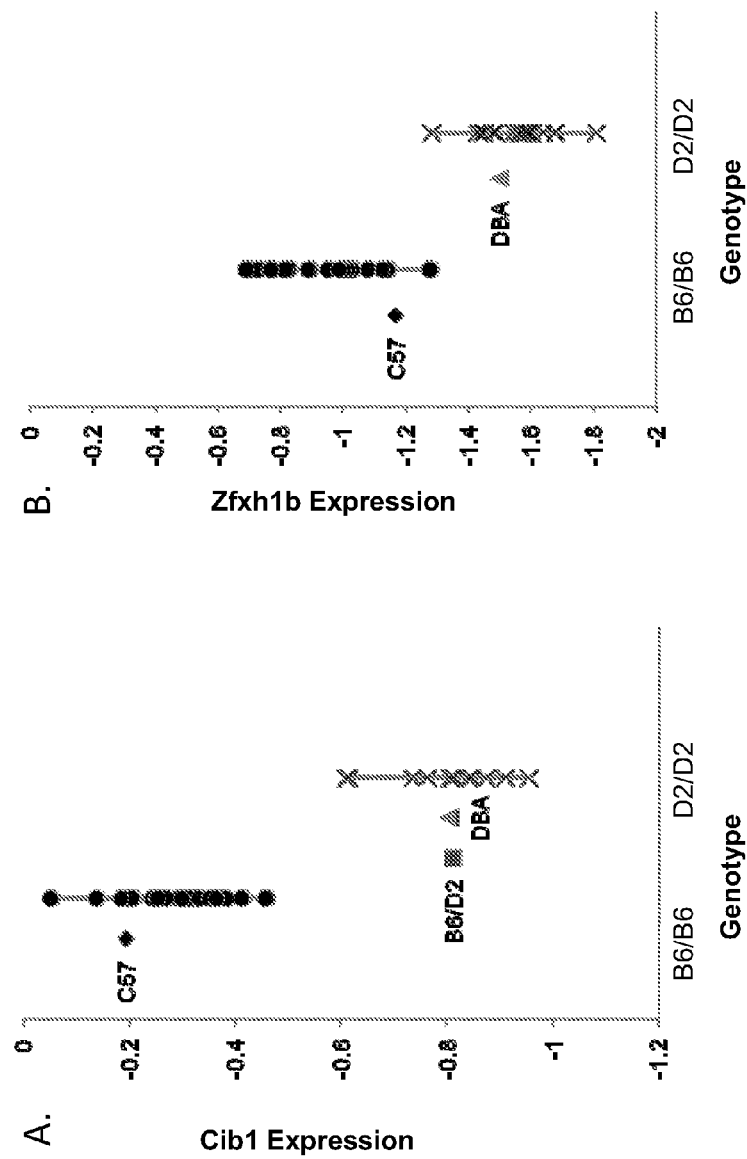
FIG. 5 shows graphs plotting of Cib1 (FIG. 5A) or Zfhx1b (FIG. 5B) genotype (B6/B6, B6/D2 or D2/D2) vs. calmyrin (FIG. 5A) or Zfhx1b (FIG. 5B) mRNA concentration in liver (arbitrary units) for 40 recombinant inbred lines, as in FIG. 1B. Data obtained from GeneNetwork.org (Wang, supra); liver data set described by Gatti, supra.

Marker rs4226715 is located on chromosome 7 at 80.138616 Mb, within the modifier locus for that chromosome. Two genes from this interval showed extremely high heritability of expression within the liver: the Ngrn gene, and the Cib1 gene. The Ngrn gene encodes neugrin, a widely expressed protein of unknown function whose expression increases in some cancers and has been associated with neuroblastoma differentiation (S. Ishigaki, et al., Biochem Biophys Res Commun 279, 526 (2002), S. R. Hustinx, et al., Cancer Biol Ther 3, 1254 (2004)), and the Cib1 gene, encodes calmyrin, a myristoylated calcium- and integrin-binding membrane-associated protein originally discovered because of its preferential interaction with presenilin 2 in HeLa cells (S. M. Stabler, et al., J Cell Biol 14, 145, 1277 (1999)). These genes showed the highest correlations: Pearson's values r=0.945, and r=−0.913, respectively, both p<4.99 e-39, (FIGS. 5 and 4, respectively). Ngrn is located on chromosome 7 at 80.138736 Mb and Cib1 at 80.101507, both consistent with the mapped modifier locus.

As noted above, calmyrin has a demonstrated interaction with presenilin 2. However, because the calmyrin distribution in the brain does not correlate well with either brain presenilin distribution or regions most susceptible to AD pathology, prior studies have considered its potential role in contributing to Aβ production in the forebrain, but judged such a role unlikely (M. Blazejczyk, et al., Biochim Biophys Acta 1762, 66 (2006)). Calmyrin is, however, highly expressed by the liver (S. M. Stabler, supra). One suggested calmyrin activity is as a protein ligand for the inositol 1,4,5-trisphosphate receptor Ca(2+) release channel (C. White, et al., J Biol Chem 281, 20825 (2006).), whose gating activity is aberrant in chicken cells transfected with mutant presenilin genes (K. H. Cheung, et al., Neuron 58, 871 (2008)).

The heritability of liver calmyrin mRNA expression was extremely high. In every strain that inherited its Cib1 genes from the B6 parents, the amount of calmyrin mRNA was higher than the amount observed in strains that inherited their Cib1 genes from the D2 parents (FIG. 5A). One strain (line 73) appears to be heterozygous at the probe, but expresses D2-like amounts of calmyrin mRNA. This suggests that low calmyrin expression in liver decreases the accumulation of Aβ in the brain, and protects mice from its adverse effects.

Treatment with a compound that decreases the Aβ-potentiating activity of calmyrin should mimic the low expression of the D2 genotype and therefore be protective.

Neugrin has an inverse correlation (FIG. 4). Abundance of neugrin in liver is correlated with lower Aβ accumulation, suggesting that treatment with a compound that increases Neugrin should be protective.

Marker rs3669981 is located on chromosome 2 at 44.943029 Mb, within the fairly broad modifier locus for that chromosome. The Zfhx1b gene (44.810557 Mb), which encodes zinc finger homeobox 1b protein, showed the highest correlation: r=−0.919, p=4.99 e-39 (FIG. 5B). The eZfhxb1 protein is a Smad-interacting transcriptional corepressor involved in Wnt and hedgehog signaling (G. Bassez, et al., Neurobiol Dis 15, 240 (2004); G. Verstappen, et al., Hum Mol Genet 17, 1175 (2008); N. Isohata, et al., Int J Cancer 125, 1212 (2009).). Detrimental variants of the gene cause the developmental disorder Mowat-Wilson syndrome, which presents with multiple congenital deficits including mental retardation (C. Zweier, et al., Am J Med Genet 108, 177 (2002)). Although the Zfhx1b mRNA is widely expressed during development, especially within the nervous system, in the adult mouse it is most highly expressed in the liver (G. Bassez, supra). The Zfhx1b gene is located on chromosome 2 at 44.810557 Mb, consistent with the mapped modifier locus. The heritability of liver mRNA expression was extremely high for this gene. In nearly every strain that inherited its Zfhx1b genes from the B6 parents the amount of Zfhx1b mRNA was greater than in strains that inherited their Zfhx1b genes from the D2 parents (FIG. 5B). Strains 12 and 36 differed in genotype at the probe but had similar mRNA levels. These data suggest that low Zfhx1b expression in liver lowers the accumulation of Aβ in the brain and protects mice from its adverse effects. Treatment with a compound that inhibits the activity of Zfhx1b should mimic the low expression of the D2 genotype and therefore be protective.

Example 3

Measurement of Aβ Inhibition by Imatinib Derivative Compositions

Figure 6:
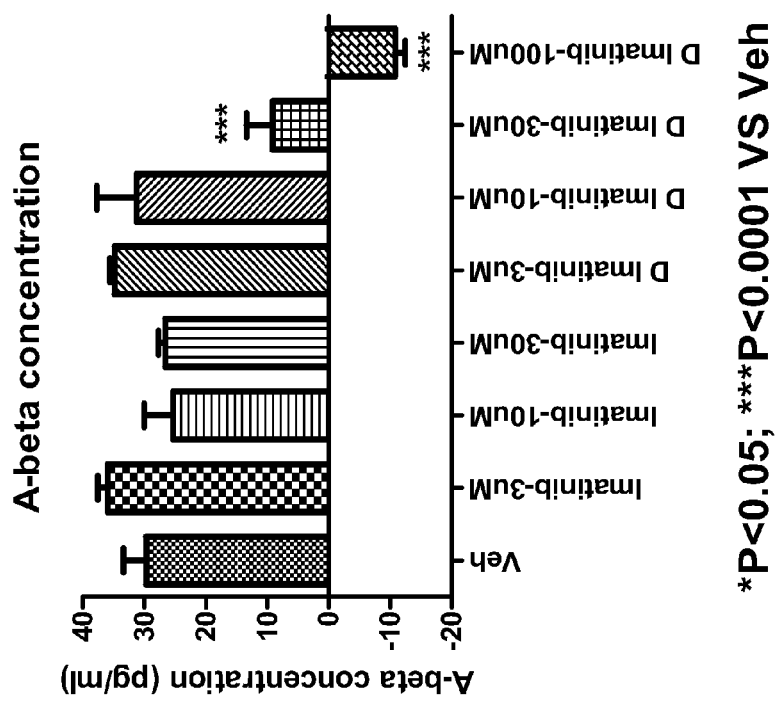
FIG. 6 shows a graph comparing the effects of imatinib and desmethyl imatinib on the concentration of Aβ in treated cells.

Protocol
1. Thaw SYSY-APP cells, add to warmed high glucose DMEM with 10% serum, pen-strep in t-75 flask. In 2 days, split culture into 4 flasks. Collect cells from 3 and freeze in liquid N2. Use remaining culture for experiment.
2. Seed 24-well plate with cells in same media. Grow to confluence.
3. Prepare stock solutions of imatinib and desmethyl imatinib:
   500 ug in 100 ul is 10 mM stock
   Also make 1 mM stock
4. Replace media (1 ml) and add inhibitor (in DMSO vehicle) or vehicle only, as follows:
   1. vehicle only
   2. 3 ul imatinib from 1 mM stock=3 uM final concentration
   3. 3 ul desmethyl imatinib (Santa Cruz Biotechnology Cat. No. SC-208027; Toronto Research Chemicals, Cat. No. D292045) from 1 mM stock=3 uM final concentration
   4. 10 ul imatinib from 1 mM stock=10 uM final concentration
   5. 10 ul desmethyl imatinib from 1 mM stock=10 uM final concentration
   6. 3 ul imatinib from 10 mM stock=30 uM final concentration
   7. 3 ul desmethyl imatinib from 10 mM stock=30 uM final concentration
   8. 10 ul desmethyl imatinib from 10 mM stock=100 uM final concentration
5. After 16 hr incubation, isolate media, add 10 ul protease inhibitor and spin out cells and debris (3000×g);
4. Measure Aβ in 100 μL aliquot with Covance ELISA kit SIG-38952, luminometer The results are shown in FIG. 6. These data show that the metabolite desmethyl imatinib (shown in FIG. 10A) produces more effective reduction of Aβ than does imatinib (Gleevec) when administered over the same range of concentration.

In addition to the above, the effect on Aβ concentration of three variants of imatinib was tested as described above, except Aβ was measured on 150 μL of media supernatant rather than 100 uL:

A. Imatinib (Gleevec) 3, 10, and 30 μM;
B. Imatinib para-diaminomethylbenzene 3 HCl (shown in FIG. 10B, Toronto Research Chemicals, Cat. No. 1267995) at 3, 10, 30, and 100 μM;
C. imatinib (pyridine)-N-oxide (shown in FIG. 10C, Toronto Research Chemicals, Cat. No. 1268010); and
D. imatinib (piperidine)-N-oxide (shown in FIG. 10D, Toronto Research Chemicals, Cat. No. 1268000).

Figure 7:
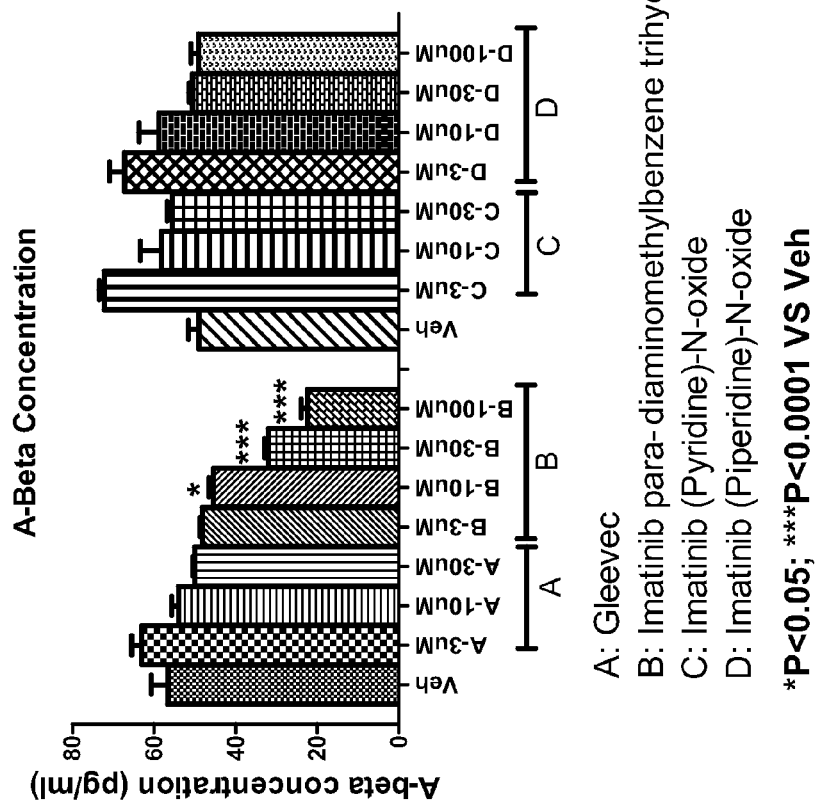
FIG. 7 shows shows a graph comparing the effects of imatinib, Imatinib para-diaminomethylbenzene 3 HCl, imatinib (pyridine)-N-oxide, and imatinib (piperidine)-N-oxide on the concentration of Aβ in treated cells.

The results are shown in FIG. 7. These data show that active metabolite Imatinib para-diaminomethylbenzene 3 HCl (shown in FIG. 10B) produces stronger inhibition of Aβ than does imatinib (Gleevec) when administered over the same range of concentration. These data also show that imatinib (pyridine)-N-oxide and imatinib (piperidine)-N-oxide have little or no effect on Aβ concentration.

Example 4

Measurement of Inhibition of Abl Kinase by Imatinib-related Compositions

The following were combined in order:
  10 μL 2.5× kinase assay buffer
  2.5 μL Abl kinase (Millipore, Temecula, Calif.)
  1 μL DMSO vehicle or inhibitor in DMSO on ice
  10 μL gamma $^{32}$P-ATP
  2.5 μL Abltide synthetic peptide substrate, biotin-tagged (Millipore, Temecula, Calif.)
Incubate at 30° C. for 10 min.;
Stop by the addition of 12.5 μL 7.5M guanidine HCL to each reaction, vortex.
Spot 12.5 μL on SAM2 biotin capture membrane (Promega Corp., Madison, Wis.)
Wash the membrane (4×2M NaCl; 4×2M NaCl, 1% $H_3PO_4$, 2×$H_2O$, at room temp.)
Kinase activity was determined by scintillation counting.
The Scintillation count: final drug concentration shown
Each assay was performed in duplicate. The counts per minute measured were as follows and the average of the two assays is shown in the right hand column:

|  | CPM | AVERAGE |
|---|---|---|
| 1. DMSO (vehicle) | 2837 | 2897 |
| 2. DMSO (vehicle) | 2956 |  |
| 1. 10 μM Gleevec | 308 | 296 |
| 2. 10 μM Gleevec | 284 |  |
| 1. 30 μM Gleevec | 145 | 126 |
| 2. 30 μM Gleevec | 107 |  |
| 1. 100 μM Gleevec | 51 | 50 |
| 2. 100 μM Gleevec | 48 |  |
| 1. 10 μM Desmethyl imatinib | 540 | 595 |
| 2 10 μM Desmethyl imatinib | 649 |  |
| 1. 30 μM Desmethyl imatinib | 149 | 149 |
| 2. 30 μM Desmethyl imatinib | lost tube |  |
| 1. 100 μM Desmethyl imatinib | 5 | 107 |
| 2. 100 μM Desmethyl imatinib | 119 |  |
| 1. 10 μM para-diaminomethylbenzene 3HCl | 2326 | 2170 |
| 2. 10 μM para-diaminomethylbenzene 3HCl | 2013 |  |
| 1. 30 μM para-diaminomethylbenzene 3HCl | 1939 | 1848 |
| 2. 30 μM para-diaminomethylbenzene 3HCl | 1756 |  |
| 1. 100 μM para-diaminomethylbenzene 3HCl | 1275 | 925 |
| 2. 100 μM para-diaminomethylbenzene 3HCl | 575 |  |
| 1. No Abltide Substrate | 13 | 11 |
| 2. No Abltide Substrate | 8 |  |

Figure 8:
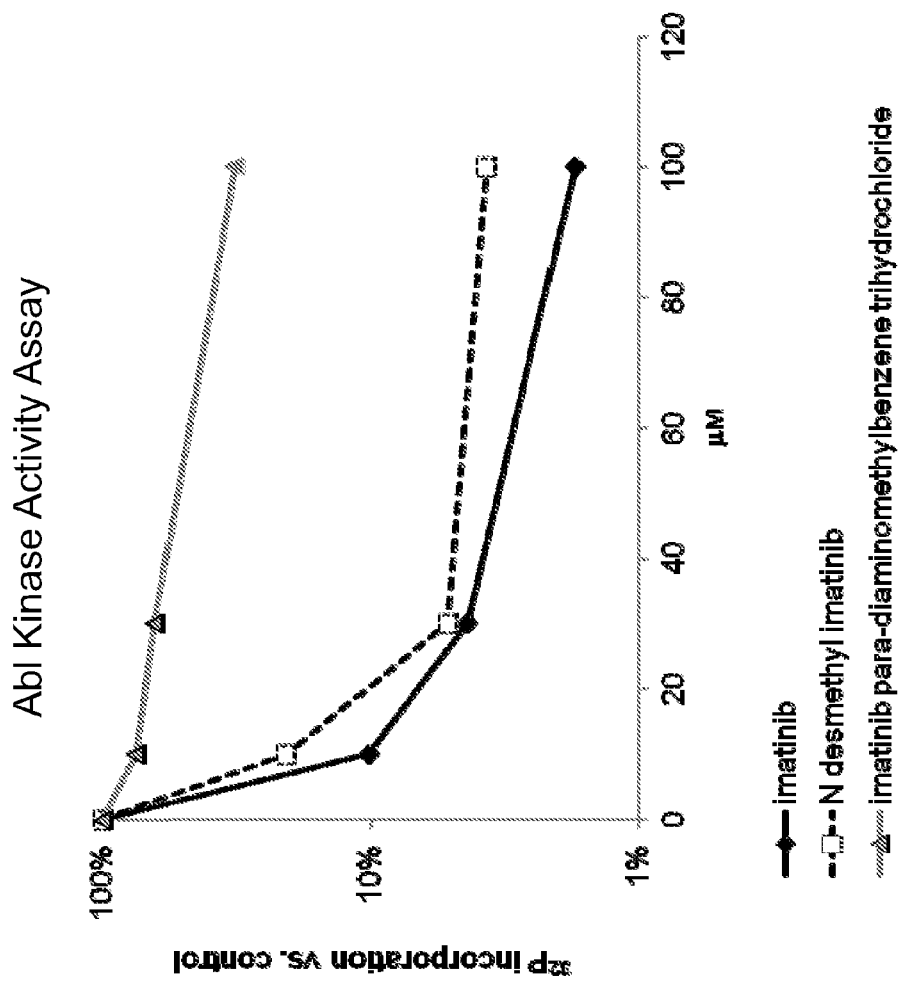
FIG. 8 shows a graph comparing the effects of imatinib, desmethyl imatinib, and imatinib para-diaminomethylbenzene on the Abl kinase activity in a cell-free assay system.
Figure 9:
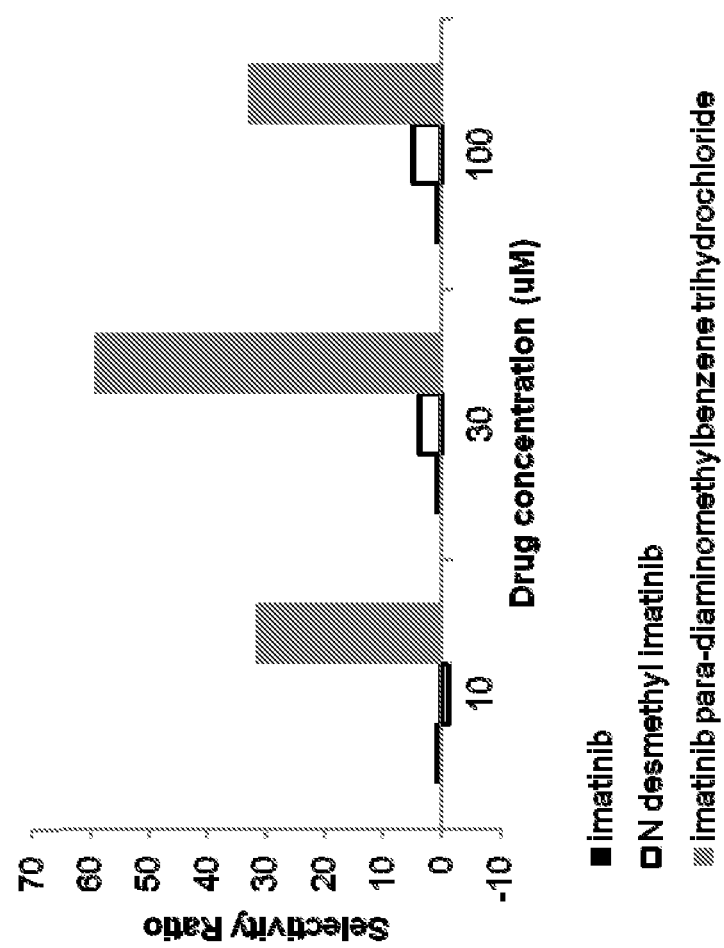
FIG. 9 shows a selectivity graph showing the ratio of the fold difference in Aβ-lowering activity for each compound (compared to imatinib) to the kinase inhibitor activity for that compound at each of the three concentrations shown.

The data are shown in FIGS. 8 and 9. FIG. 8 shows a semilog graph plot of measured Abl kinase activity in the presence of each of the drugs at concentrations from 0 to 100 μM. Imatinib substantially inhibits Abl kinase even at the lowest concentration tested, 10 μM. N-desmethyl imatinib inhibits Abl kinase less than does imatinib, and treatment with imatinib para-diaminomethylbenzene trihydrochloride shows a markedly lower level of Abl kinase inhibition even at the highest concentration tested, 100 μM.

FIG. 9 shows a selectivity graph showing the ratio of the fold difference in Aβ-lowering activity for each compound (compared to imatinib) to the kinase inhibitor activity for that compound at each of the three concentrations shown. Imatinib is the reference compound so the ratio value for this drug is set to 1.

N-desmethyl imatinib shows 3.8 to 4.8-fold improvement over imatinib in selectivity. Imatinib para-diaminomethylbenzene trihydrochloride showed the greatest selectivity. At the 30 μM concentration, the paradiaminobenzene composition exhibited about a 3.7 fold greater activity in lowering Aβ, with only $\frac{1}{16}^{th}$ of the activity of imatinib in the Abl kinase assay, resulting in a selectivity ratio of nearly 60.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of treating a subject having a brain Aβ disorder or predisposition to a brain Aβ disorder, comprising peripherally administering an effective amount of imatinib para-diaminomethylbenzene or a pharmaceutically acceptable salt of imatinib para-diaminomethylbenzene to modulate production of Aβ in a peripheral tissue of said subject.

2. The method of claim 1, wherein the brain Aβ disorder is Alzheimer's disease.

3. The method of claim 1, wherein said modulation comprises reducing production of Aβ in said peripheral tissue.

4. The method of claim 1, wherein said peripheral tissue is liver.

5. The method of claim 1, wherein said imatinib para-diaminomethylbenzene is in the form of a mesylate salt.

6. The method of claim 1, wherein said imatinib para-diaminomethylbenzene or a pharmaceutically acceptable salt thereof is administered in a composition that further comprises a known therapeutic agent for treating, ameliorating, or reducing risk or severity of a brain Aβ-related disorder.

7. The method of claim 6, wherein said known therapeutic agent is selected from the group consisting of imatinib, cannabinoids, dimebom, prednisone, ibuprofen, naproxyn, indomethacin; statins, selective estrogen receptor molecules, antihypertensives, alpha-blockers, beta-blockers, alpha-beta blockers, angiotensin-converting enzyme inhibitors, angiotensin receptor blockers, calcium channel blockers, diuretics, NSAIDS, and antioxidants.

8. The method of claim 1, wherein said peripherally administering comprises orally administering.

* * * * *